(12) United States Patent
Gross

(10) Patent No.: US 11,565,104 B1
(45) Date of Patent: Jan. 31, 2023

(54) MAGNETICALLY-DRIVEN RECIPROCATING INTRAVASCULAR BLOOD PUMP

(71) Applicant: RAINBOW MEDICAL LTD., Herzliya (IL)

(72) Inventor: Yossi Gross, Moshav Mazor (IL)

(73) Assignee: YOSSI GROSS, Moshav Mazor (IL)

( * ) Notice: Subject to any disclaimer, the term of this patent is extended or adjusted under 35 U.S.C. 154(b) by 0 days.

(21) Appl. No.: 17/397,404

(22) Filed: Aug. 9, 2021

(51) Int. Cl.
| | |
|---|---|
| *A61F 2/24* | (2006.01) |
| *A61M 60/459* | (2021.01) |
| *A61M 60/884* | (2021.01) |
| *A61M 60/139* | (2021.01) |
| *A61M 60/274* | (2021.01) |
| *A61M 60/531* | (2021.01) |
| *A61M 60/515* | (2021.01) |
| *A61M 60/17* | (2021.01) |

(52) U.S. Cl.
CPC ......... *A61M 60/884* (2021.01); *A61F 2/2418* (2013.01); *A61M 60/139* (2021.01); *A61M 60/17* (2021.01); *A61M 60/274* (2021.01); *A61M 60/459* (2021.01); *A61M 60/515* (2021.01); *A61M 60/531* (2021.01)

(58) Field of Classification Search
CPC ........................... A61M 60/884; A61M 60/459
See application file for complete search history.

(56) References Cited

U.S. PATENT DOCUMENTS

| | | |
|---|---|---|
| 3,842,440 A | 10/1974 | Karlson |
| 4,102,610 A | 7/1978 | Taboada et al. |
| 4,245,294 A * | 1/1981 | Brolin ................. H04M 19/008 363/126 |
| 4,541,787 A | 9/1985 | DeLong |
| 4,610,658 A | 9/1986 | Buchwald et al. |
| 4,965,864 A | 10/1990 | Roth et al. |
| 5,089,017 A | 2/1992 | Young et al. |
| 5,484,385 A | 1/1996 | Rishton |

(Continued)

FOREIGN PATENT DOCUMENTS

WO 2020/081481 A1 4/2020

OTHER PUBLICATIONS

An Office Action dated Jun. 27, 2019, which issued during the prosecution of U.S. Appl. No. 15/831,973.

(Continued)

*Primary Examiner* — Jacqueline Woznicki
(74) *Attorney, Agent, or Firm* — Sughrue Mion, PLLC

(57) ABSTRACT

A mechanical circulatory assist device is provided including a stent, a coiled wire wound around the stent, and a reciprocating valve including a housing, one or more leaflets coupled to the housing, and one or more permanent magnets coupled to the housing. The magnets are arranged to interact with a magnetic field generated by the coiled wire when current flows therethrough, so as to axially move the reciprocating valve with respect to the stent when the reciprocating valve is disposed within the stent. Upstream axial motion of the reciprocating valve causes the leaflets to be in an open state in which they allow blood flow through the reciprocating valve. Downstream axial motion of the reciprocating valve causes the leaflets to be in a closed state in which they inhibit blood flow through the reciprocating valve. Other embodiments are also described.

37 Claims, 15 Drawing Sheets

(56) References Cited

U.S. PATENT DOCUMENTS

| | | | |
|---|---|---|---|
| 5,527,159 A * | 6/1996 | Bozeman, Jr. | F04B 49/06 |
| | | | 417/244 |
| 5,693,091 A | 12/1997 | Larson, Jr. et al. | |
| 5,762,599 A | 6/1998 | Sohn | |
| 5,928,280 A * | 7/1999 | Hansen | A61F 2/915 |
| | | | 600/36 |
| 6,123,723 A * | 9/2000 | Konya | A61F 2/90 |
| | | | 623/1.11 |
| 6,290,641 B1 | 9/2001 | Nigroni et al. | |
| 7,229,258 B2 * | 6/2007 | Wood | A61M 60/148 |
| | | | 417/355 |
| 7,468,050 B1 | 12/2008 | Kantrowitz | |
| 7,544,160 B2 | 6/2009 | Gross | |
| 7,722,568 B2 | 5/2010 | Lenker et al. | |
| 7,976,452 B2 | 7/2011 | Kantrowitz | |
| 8,690,749 B1 * | 4/2014 | Nunez | A61M 60/205 |
| | | | 600/16 |
| 8,900,191 B2 | 12/2014 | Lenker et al. | |
| 8,986,376 B2 | 3/2015 | Solem | |
| 9,061,162 B2 | 6/2015 | Mashiach et al. | |
| 10,881,771 B2 | 1/2021 | Solem | |
| 2003/0032853 A1 | 2/2003 | Korakianitis et al. | |
| 2008/0284386 A1 * | 11/2008 | Nishimura | H02P 9/102 |
| | | | 322/28 |
| 2009/0017088 A1 * | 1/2009 | Klocke | A61F 2/82 |
| | | | 424/422 |
| 2011/0037327 A1 * | 2/2011 | Denne | H02K 41/03 |
| | | | 310/12.16 |
| 2013/0240905 A1 * | 9/2013 | Hobart | H01L 29/66143 |
| | | | 257/77 |
| 2016/0206798 A1 | 7/2016 | Williams et al. | |
| 2017/0274128 A1 * | 9/2017 | Tamburino | A61M 60/892 |
| 2018/0326132 A1 | 11/2018 | Maimon et al. | |
| 2019/0167877 A1 * | 6/2019 | Gross | A61M 60/50 |
| 2019/0255236 A1 | 8/2019 | Gross | |
| 2021/0085846 A1 | 3/2021 | Ayre et al. | |
| 2021/0288581 A1 * | 9/2021 | Zhu | H02M 3/1586 |

OTHER PUBLICATIONS

European Search Report dated Dec. 19, 2019 which issued during the prosecution of Applicant's European App No. 19178111.1.

Notice of Allowance dated Oct. 9, 2019, which issued during the prosecution of U.S. Appl. No. 15/831,973.

"Voice coil actuators vs solenoids: What is the difference?" Aerospace Manufacturing and Design, Oct. 28, 2015 (7 pages).

Non-Final Office Action issued in U.S. Appl. No. 16/399,101, dated Oct. 6, 2020.

* cited by examiner

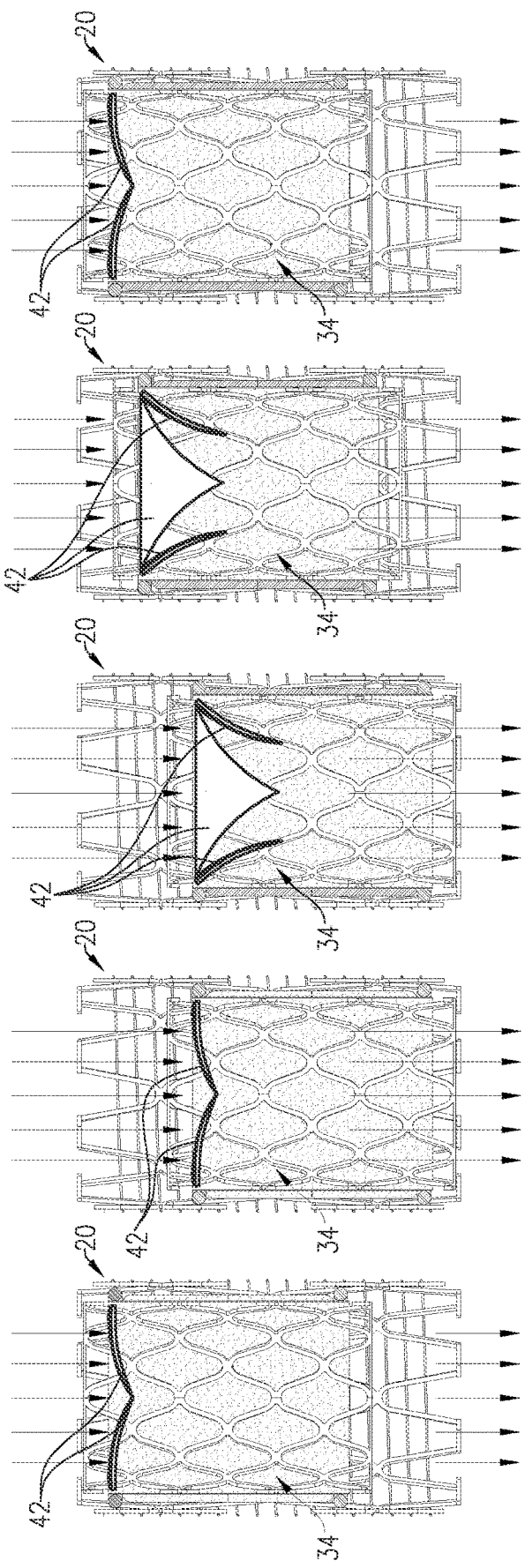

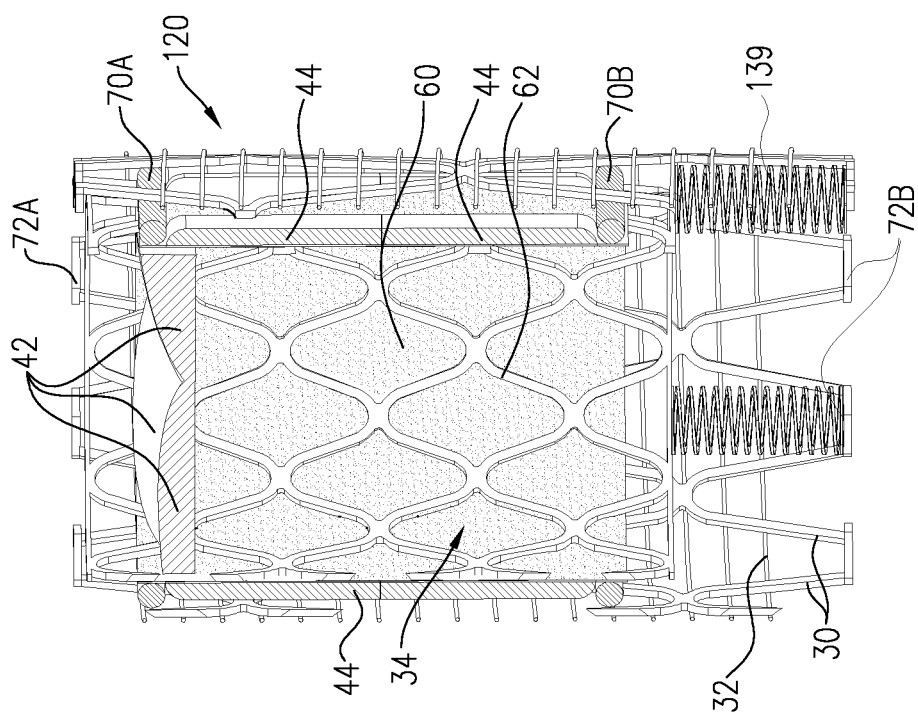
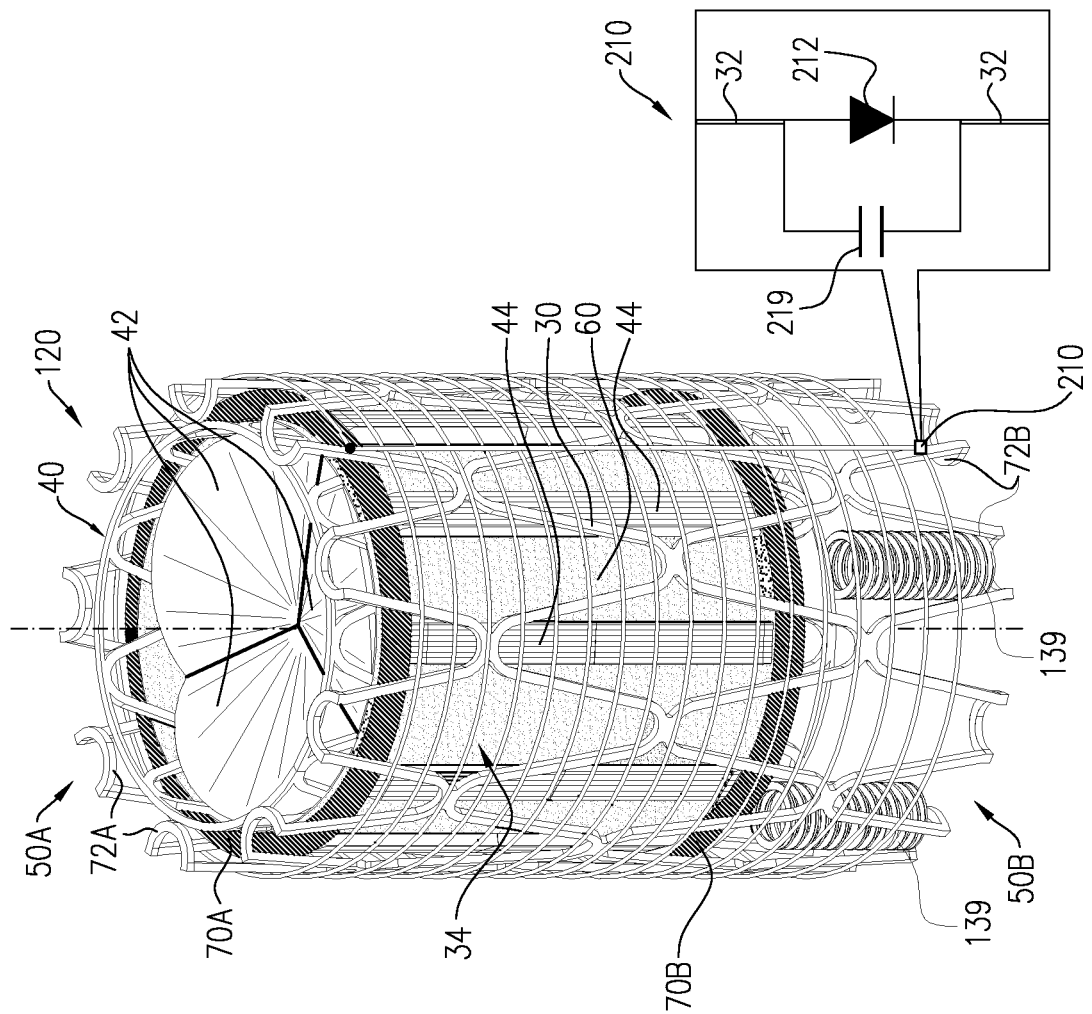
FIG. 8B
FIG. 8A

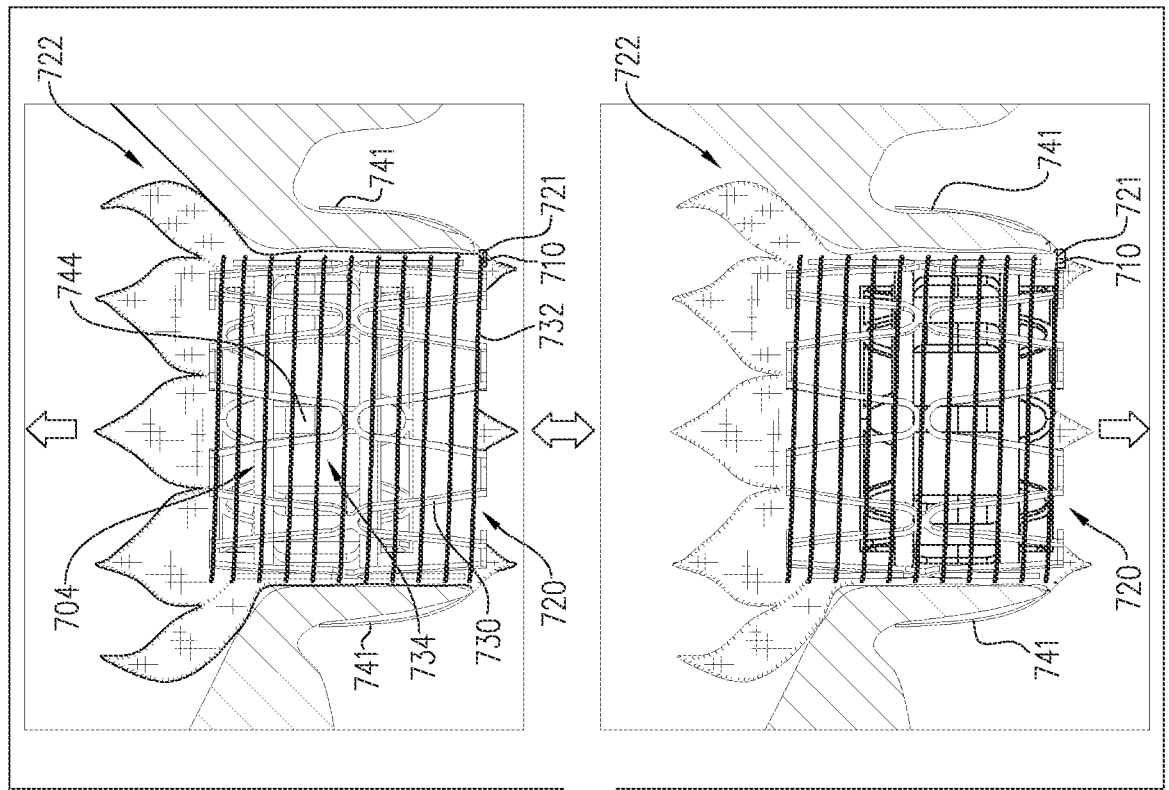
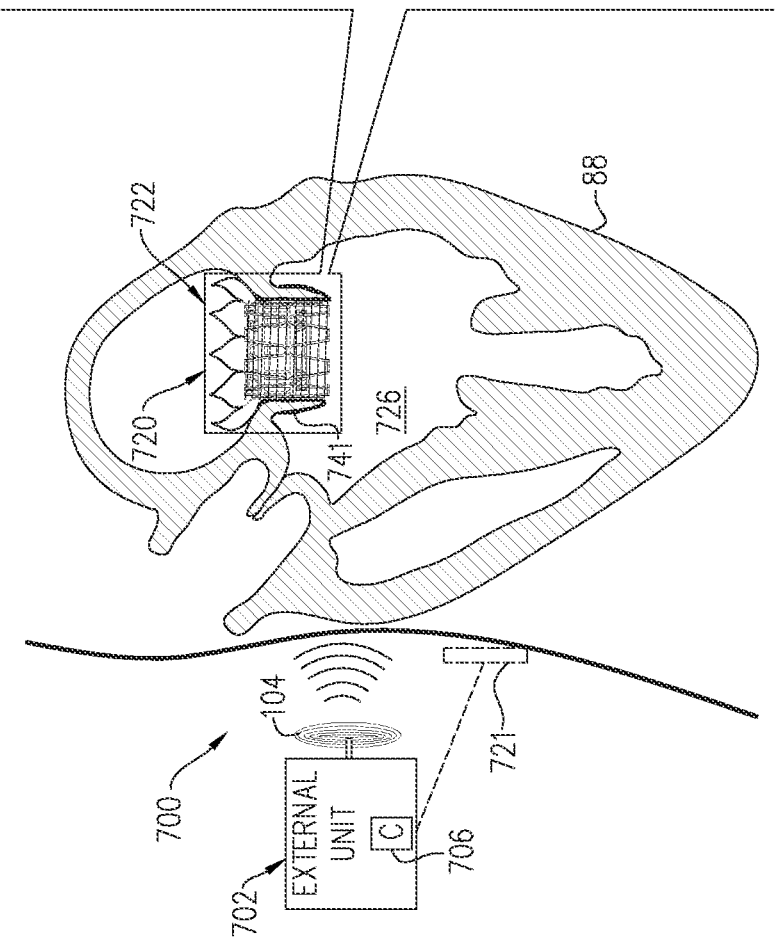
FIG. 13

MAGNETICALLY-DRIVEN RECIPROCATING INTRAVASCULAR BLOOD PUMP

FIELD OF THE INVENTION

Some applications of the invention relate generally to medical procedures and implantable devices. More specifically, some applications of the invention relate to the use of a mechanical device for deployment in the circulatory system.

BACKGROUND

Cardiovascular disease is one of the leading causes of death. Blood pumps for insertion into the vasculature of a patient have been developed to provide mechanical circulatory support by supplementing the blood pumping action of a damaged or diseased heart. An example of an intravascular blood pump is the intra-aortic balloon pump, which is a pneumatic device typically deployed in an aorta of a patient to augment the pumping action of the heart. Typically, the aortic balloon pump includes a balloon, which inflates and deflates in a predetermined synchronous pattern with respect to the diastole and systole of the patient (inflates during diastole and deflates during systole). The aortic balloon pump typically inflates during diastole, thereby increasing coronary flow in the coronary arteries, and deflates during systole, thereby increasing blood flow forward in the aorta.

U.S. Pat. No. 10,568,999 to Gross, which is incorporated herein by reference, describes apparatus for deployment in a lumen of a blood vessel of a subject. The apparatus includes a reciprocating device configured to move downstream and upstream in the blood vessel in a reciprocating pattern to provide: (i) a first effective surface area of the device for pushing blood downstream in the blood vessel during downstream motion of the reciprocating device, and (ii) second effective surface area of the device during upstream motion of the reciprocating device. The first effective surface area is larger for pushing blood in the blood vessel than the second effective surface area. The apparatus further includes a device driver configured to drive the reciprocating device in the reciprocating pattern.

U.S. Pat. No. 11,013,906 to Gross, which is incorporated herein by reference, describes apparatus that is configured to be deployed in a lumen of a blood vessel of a subject. The apparatus includes a pump portion, including an anchor configured to engage a wall of the blood vessel in order to maintain the apparatus in place within the blood vessel, and a reciprocating valve coupled to the anchor and including a set of one or more leaflets. A valve driver is configured to drive the reciprocating valve in a reciprocating pattern between (i) a first state in which the leaflets are in an open configuration allowing blood flow through the reciprocating valve, and (ii) a second state in which the leaflets are in a closed configuration inhibiting blood flow through the reciprocating valve.

SUMMARY OF THE APPLICATION

In accordance with some applications of the present invention, a mechanical circulatory assist device is provided for deployment in a cardiovascular system of a subject. The device typically affects blood flow in the cardiovascular system and improves circulation. The device may thus be useful for treating heart failure, among other conditions.

The mechanical circulatory assist device comprises a stent and a coiled wire wound around the stent. The stent and the coiled wire are configured to assume a radially-compressed configuration and a radially-expanded configuration. The coiled wire is configured to generate a magnetic field when current flows through the coiled wire when the stent and the coiled wire are in the radially-expanded configuration of the stent and the coiled wire.

The mechanical circulatory assist device further comprises a reciprocating valve, which is configured to assume radially-compressed and radially-expanded configurations. The reciprocating valve comprises a housing, one or more leaflets coupled to the housing, and one or more permanent magnets coupled to the housing. The one or more permanent magnets are arranged to interact with the magnetic field generated by the coiled wire, so as to axially move the reciprocating valve with respect to the stent when the reciprocating valve is in the radially-expanded configuration of the reciprocating valve disposed within the stent when the stent and the coiled wire are in the radially-expanded configuration of the stent and the coiled wire.

The reciprocating valve is configured such that:
upstream axial motion of the reciprocating valve causes the one or more leaflets to be in an open state in which the one or more leaflets allow blood flow through the reciprocating valve, and
downstream axial motion of the reciprocating valve causes the one or more leaflets to be in a closed state in which the one or more leaflets inhibit blood flow through the reciprocating valve.

The reciprocating valve typically affects blood flow in the cardiovascular system by reciprocation between:
the closed state of the one or more leaflets in which downstream axial motion of the reciprocating valve pushes blood downstream in the cardiovascular system, thereby assisting functioning of the heart, and
the open state of the one or more leaflets in which upstream axial motion of the reciprocating valve has minimal effect on blood flow.

The mechanical circulatory assist device may function as a positive displacement pump having high efficiency.

For example, the mechanical circulatory assist device may be deployed in the aorta at a location that is downstream of the native aortic valve, e.g., in the descending aorta. Operation of the mechanical circulatory assist device in the aorta increases blood flow in the aorta and reduces pressure in the ascending aorta (upstream of the reciprocating valve).

Typically, the coiled wire and the one or more permanent magnets are arranged and operated using certain principles of a voice coil, which, as known in the engineering arts, is a linear actuator that provides a constant linear force and constant movement over the stroke, and can move bi-directionally.

The radial compressibility of the stent, the coiled wire, and the reciprocating valve allow the mechanical circulatory assist device to be delivered in a transcatheter, non-open surgery procedure. Typically, the reciprocating valve is configured to be inserted into the stent while in the radially-compressed configuration of the reciprocating valve, after the stent has been deployed and radially expanded in the cardiovascular system. This in vivo assembly of the mechanical circulatory assist device allows the stent and the coiled wire, on the one hand, and the reciprocating valve, on the other hand, to be delivered and deployed separately from first and second delivery sheath longitudinal segments, which may be portions of separate delivery sheaths or a single delivery sheath.

There is therefore provided, in accordance with an Inventive Concept 1 of the present invention, a mechanical circulatory assist device configured to be deployed in a cardiovascular system of a subject, the mechanical circulatory assist device including:
(a) a stent;
(b) a coiled wire, which is wound around the stent inside, outside, or partially inside and partially outside the stent, wherein the stent and the coiled wire are configured to assume a radially-compressed configuration and a radially-expanded configuration, and wherein the coiled wire is configured to generate a magnetic field when current flows through the coiled wire when the stent and the coiled wire are in the radially-expanded configuration of the stent and the coiled wire; and
(c) a reciprocating valve, which is configured to assume radially-compressed and radially-expanded configurations, and which includes:
  (i) a housing;
  (ii) one or more leaflets, coupled to the housing; and
  (iii) one or more permanent magnets, which are coupled to the housing, and are arranged to interact with the magnetic field generated by the coiled wire, so as to axially move the reciprocating valve with respect to the stent when the reciprocating valve is in the radially-expanded configuration of the reciprocating valve disposed within the stent when the stent and the coiled wire are in the radially-expanded configuration of the stent and the coiled wire, wherein the reciprocating valve is configured such that:
  upstream axial motion of the reciprocating valve causes the one or more leaflets to be in an open state in which the one or more leaflets allow blood flow through the reciprocating valve, and
  downstream axial motion of the reciprocating valve causes the one or more leaflets to be in a closed state in which the one or more leaflets inhibit blood flow through the reciprocating valve.

Inventive Concept 2. The mechanical circulatory assist device according to Inventive Concept 1, wherein the one or more permanent magnets are arranged to interact with the magnetic field generated by the coiled wire, so as to axially slide the reciprocating valve with respect to the stent when the reciprocating valve is in the radially-expanded configuration of the reciprocating valve disposed within the stent when the stent and the coiled wire are in the radially-expanded configuration of the stent and the coiled wire.

Inventive Concept 3. The mechanical circulatory assist device according to Inventive Concept 1, wherein the reciprocating valve is configured to be inserted into the stent when the stent and the coiled wire are in the radially-expanded configuration of the stent and the coiled wire and the reciprocating valve is in the radially-compressed configuration of the reciprocating valve.

Inventive Concept 4. The mechanical circulatory assist device according to Inventive Concept 1, wherein the reciprocating valve includes 10-20 permanent magnets.

Inventive Concept 5. The mechanical circulatory assist device according to Inventive Concept 1, wherein the housing has a housing length when the reciprocating valve is in the radially-expanded configuration of the reciprocating valve, and wherein the one or more permanent magnets have an average magnet length of 70%-100% of the housing length.

Inventive Concept 6. The mechanical circulatory assist device according to Inventive Concept 1, wherein the housing has a housing length when the reciprocating valve is in the radially-expanded configuration of the reciprocating valve, wherein the stent has a stent length when the stent and the coiled wire are in the radially-expanded configuration of the stent and the coiled wire, and wherein the housing length is 50% — 90% of the stent length.

Inventive Concept 7. The mechanical circulatory assist device according to Inventive Concept 1, wherein the housing has a housing outer diameter when the reciprocating valve is in the radially-expanded configuration of the reciprocating valve, wherein the stent has a stent inner diameter when the stent and the coiled wire are in the radially-expanded configuration of the stent and the coiled wire, and wherein the housing outer diameter is 80%-95% of the stent inner diameter.

Inventive Concept 8. The mechanical circulatory assist device according to Inventive Concept 1, wherein, when the stent and the coiled wire are in the radially-expanded configuration of the stent and the coiled wire:
  the stent has a stent length, and
  the coiled wire has a coil axial length, measured along an axis of the stent, of 50%-90% of the stent length.

Inventive Concept 9. The mechanical circulatory assist device according to Inventive Concept 8, wherein the housing has a housing length when the reciprocating valve is in the radially-expanded configuration of the reciprocating valve, and wherein the one or more permanent magnets have an average magnet length of 70% — 100% of the housing length.

Inventive Concept 10. The mechanical circulatory assist device according to Inventive Concept 1, wherein, when the reciprocating valve is in the radially-expanded configuration of the reciprocating valve and the stent and the coiled wire are in the radially-expanded configuration of the stent and the coiled wire:
  the housing has a housing length, and
  the coiled wire has a coil axial length, measured along an axis of the stent, of 50%-100% of the housing length.

Inventive Concept 11. The mechanical circulatory assist device according to Inventive Concept 1, wherein, when the reciprocating valve is in the radially-expanded configuration of the reciprocating valve and the stent and the coiled wire are in the radially-expanded configuration of the stent and the coiled wire:
  the coiled wire has a coil axial length, measured along an axis of the stent, and
  the one or more permanent magnets have an average magnet length of 60%-100% of the coil axial length.

Inventive Concept 12. The mechanical circulatory assist device according to Inventive Concept 1, wherein the coiled wire is shaped so as to define 10-100 wire turns.

Inventive Concept 13. The mechanical circulatory assist device according to Inventive Concept 1, wherein the coiled wire is shaped so as to have a pitch of 0.2-2 mm.

Inventive Concept 14. The mechanical circulatory assist device according to Inventive Concept 1, wherein the mechanical circulatory assist device does not include any active electronic components.

Inventive Concept 15. The mechanical circulatory assist device according to any one of Inventive Concepts 1-14, wherein the mechanical circulatory assist device is configured to be deployed in a blood vessel of the cardiovascular system.

Inventive Concept 16. The mechanical circulatory assist device according to Inventive Concept 15, wherein the stent is configured to anchor the mechanical circulatory assist device to a wall of the blood vessel.

Inventive Concept 17. The mechanical circulatory assist device according to Inventive Concept 15, wherein the blood vessel is an aorta of the subject, and wherein the mechanical circulatory assist device is configured to be deployed in the aorta.

Inventive Concept 18. The mechanical circulatory assist device according to any one of Inventive Concepts 1-14, wherein the mechanical circulatory assist device is configured to be deployed at a mitral valve of the cardiovascular system.

Inventive Concept 19. A mechanical circulatory assist system comprising the mechanical circulatory assist device according to Inventive Concept 18,
wherein the coiled wire is configured such that the current is electromagnetically induced in the coiled wire when the coiled wire is subjected to a time-varying magnetic field generated outside a body of the subject when the stent and the coiled are in the radially-expanded configuration of the stent and the coiled wire, with the mechanical circulatory assist device deployed at the mitral valve,
wherein the mechanical circulatory assist system further includes an external unit, which includes:
an external coil, which is configured to be placed outside the body of the subject; and
external-unit control circuitry, which is configured to drive the external coil to generate the time-varying magnetic field,
wherein the mechanical circulatory assist system includes a sensor configured to sense at least one physiological parameter correlated with a cardiac cycle of the subject, and
wherein the mechanical circulatory assist system is configured to coordinate pumping of the reciprocating valve with the at least one physiological parameter sensed by the sensor.

Inventive Concept 20. The mechanical circulatory assist system according to Inventive Concept 19, wherein the at least one physiological parameter includes a left ventricular pressure.

Inventive Concept 21. The mechanical circulatory assist system according to Inventive Concept 19, wherein the at least one physiological parameter includes a feature of an electrocardiogram.

Inventive Concept 22. The mechanical circulatory assist system according to Inventive Concept 19, wherein the mechanical circulatory assist system is configured to activate motion of the reciprocating valve only during all or a portion of diastole, as detected using the sensor.

Inventive Concept 23. The mechanical circulatory assist system according to Inventive Concept 22, wherein the mechanical circulatory assist system is configured to activate the motion of the reciprocating valve in a plurality of strokes during diastole of each cardiac cycle, wherein each of the strokes includes the upstream axial motion and the downstream axial motion of the reciprocating valve.

Inventive Concept 24. A mechanical circulatory assist system comprising the mechanical circulatory assist device according to Inventive Concept 18,
wherein the coiled wire is configured such that the current is electromagnetically induced in the coiled wire when the coiled wire is subjected to a time-varying magnetic field generated outside a body of the subject when the stent and the coiled are in the radially-expanded configuration of the stent and the coiled wire, with the mechanical circulatory assist device deployed at the mitral valve,
wherein the mechanical circulatory assist system further includes an external unit, which includes:
an external coil, which is configured to be placed outside the body of the subject; and
external-unit control circuitry, which is configured to drive the external coil to generate the time-varying magnetic field, and which is not configured to drive the external coil to generate the time-varying magnetic field in coordination with a cardiac cycle of the subject.

Inventive Concept 25. The mechanical circulatory assist system according to Inventive Concept 24, wherein the mechanical circulatory assist system does not include any sensor of heart rate or the cardiac cycle.

Inventive Concept 26. The mechanical circulatory assist device according to any one of Inventive Concepts 1-14, wherein the coiled wire is configured such that the current is electromagnetically induced in the coiled wire when the coiled wire is subjected to a time-varying magnetic field generated outside a body of the subject when the stent and the coiled are in the radially-expanded configuration of the stent and the coiled wire, with the mechanical circulatory assist device deployed in the cardiovascular system.

Inventive Concept 27. The mechanical circulatory assist device according to Inventive Concept 26, further including:
a circuit in electrical communication with the coiled wire;
first and second passive diodes, which are (a) arranged in parallel along respective first and second branches of the circuit, and (b) configured to rectify the current in the respective branches in respective opposite first and second directions; and
a switch, which is arranged to selectively assume first and second states, in which the switch electrically couples only the first branch and only the second branch, respectively, to the coiled wire.

Inventive Concept 28. The mechanical circulatory assist device according to Inventive Concept 27, wherein the switch includes an electromagnetic switch, which is controllable from outside the body of the subject.

Inventive Concept 29. The mechanical circulatory assist device according to Inventive Concept 26, further including:
a passive diode, which is coupled in electrical communication with the coiled wire, and is configured to rectify the current in the coiled wire such that the one or more permanent magnets interact with the magnetic field generated by the coiled wire, so as to axially move the reciprocating valve in a first direction with respect to the stent; and
one or more springs, which are coupled to the reciprocating valve and the stent, and are arranged to:
store elastic energy during axial movement of the reciprocating valve in the first direction during interaction of the one or more permanent magnets with the magnetic field generated by the coiled wire, and
axially move the reciprocating valve in a second direction, opposite the first direction, with respect to the stent upon release of the stored elastic energy when the current does not flow through the coiled wire.

Inventive Concept 30. A mechanical circulatory assist system including the mechanical circulatory assist device according to Inventive Concept 26, the mechanical circulatory assist system further including an external unit, which includes:
an external coil, which is configured to be placed outside the body of the subject; and
external-unit control circuitry, which is configured to drive the external coil to generate the time-varying magnetic field.

Inventive Concept 31. The mechanical circulatory assist system according to Inventive Concept 30, wherein the external-unit control circuitry is configured to drive the external coil to generate the time-varying magnetic field at a frequency of 5.6-14 MHz.

Inventive Concept 32. The mechanical circulatory assist system according to Inventive Concept 30, wherein the external-unit control circuitry is configured to drive the external coil to generate the time-varying magnetic field such that the reciprocating valve reciprocates at a frequency of 2-5 Hz.

Inventive Concept 33. The mechanical circulatory assist system according to Inventive Concept 30, wherein the external-unit control circuitry is configured to drive the external coil to generate the time-varying magnetic field such that the reciprocating valve pushes blood at a rate of 600-1200 cc per minute.

Inventive Concept 34. The mechanical circulatory assist system according to Inventive Concept 30, wherein the external-unit control circuitry is not configured to drive the external coil to generate the time-varying magnetic field in coordination with a cardiac cycle of the subject.

Inventive Concept 35. The mechanical circulatory assist system according to Inventive Concept 30, wherein the mechanical circulatory assist system does not include any sensor of heart rate or cardiac cycle.

Inventive Concept 36. The mechanical circulatory assist system according to Inventive Concept 30,
  wherein the mechanical circulatory assist device further includes:
    a circuit in electrical communication with the coiled wire;
    first and second passive diodes, which are (a) arranged in parallel along respective first and second branches of the circuit, and (b) configured to rectify the current in the respective branches in respective opposite first and second directions; and
    a switch, which is arranged to selectively assume first and second states, in which the switch electrically couples only the first branch and only the second branch, respectively, to the coiled wire, and
    wherein the external-unit control circuitry is configured to cyclically drive the switch to switch between the first state and the second state.

Inventive Concept 37. A mechanical circulatory assist system including the mechanical circulatory assist device according to any one of Inventive Concepts 1-14, the mechanical circulatory assist system further including implantable control circuitry, which is in wired electrical connection with the coiled wire, and is configured to generate the current in the coiled wire.

Inventive Concept 38. The mechanical circulatory assist system according to any one of Inventive Concepts 1-14, wherein the reciprocating valve includes two or more leaflets, coupled to the housing.

Inventive Concept 39. The mechanical circulatory assist system according to Inventive Concept 38, wherein the reciprocating valve includes 2-6 leaflets, coupled to the housing.

Inventive Concept 40. The mechanical circulatory assist device according to any one of Inventive Concepts 1-14,
  wherein the stent has upstream and downstream ends,
  wherein the one or more permanent magnets have one or more respective pairs of opposite first poles and second poles, and
  wherein the one or more permanent magnets are oriented such that the first poles are closer to the upstream end of the housing than the second poles are to the upstream end of the housing.

Inventive Concept 41. The mechanical circulatory assist device according to any one of Inventive Concepts 1-14, wherein, when the stent and the coiled wire are in the radially-expanded configuration of the stent and the coiled wire:
  the coiled wire is shaped so as to define a plurality of wire turns, and
  the wire turns are shaped so as to define respective pluralities of peaks and troughs, which are aligned with the respective peaks and troughs of longitudinally adjacent wire turns.

Inventive Concept 42. The mechanical circulatory assist device according to Inventive Concept 41, wherein the pluralities of peaks and troughs are shaped so as to define respective zigzags.

Inventive Concept 43. The mechanical circulatory assist device according to any one of Inventive Concepts 1-14, wherein the stent includes interconnected stent struts arranged so as to define interconnected stent cells.

Inventive Concept 44. The mechanical circulatory assist device according to any one of Inventive Concepts 1-14, wherein the reciprocating valve further includes a blood-proof membrane that is tubular when the reciprocating valve is in the radially-expanded configuration of the reciprocating valve.

Inventive Concept 45. The mechanical circulatory assist device according to any one of Inventive Concepts 1-14, wherein the housing is cylindrical when in the radially-expanded configuration of the reciprocating valve.

Inventive Concept 46. The mechanical circulatory assist device according to Inventive Concept 45, wherein the stent is an outer stent, and wherein the housing includes a housing stent including interconnected stent struts arranged so as to define interconnected stent cells.

Inventive Concept 47. The mechanical circulatory assist device according to Inventive Concept 45, wherein, when the reciprocating valve is in the radially-expanded configuration of the reciprocating valve:
  the one or more permanent magnets have one or more respective widths, measured around a circumference of the housing, and
  a sum of the one or more widths subtends 90-150 degrees of a circumference of the housing.

Inventive Concept 48. The mechanical circulatory assist device according to any one of Inventive Concepts 1-14, wherein the stent, when the stent and the coiled wire are in the radially-expanded configuration of the stent and the coiled wire, is shaped so as to define one or more upstream stoppers, which are configured to limit the upstream axial motion of the reciprocating valve when in the radially-expanded configuration of the reciprocating valve disposed within the stent.

Inventive Concept 49. The mechanical circulatory assist device according to Inventive Concept 48, wherein the stent includes interconnected stent struts arranged so as to define interconnected stent cells, and wherein some of the stent struts are bent radially inward so as to define the one or more upstream stoppers.

Inventive Concept 50. The mechanical circulatory assist device according to Inventive Concept 48, wherein the reciprocating valve further includes an upstream seal that is annular when the reciprocating valve is in the radially-expanded configuration of the reciprocating valve, and wherein the one or more upstream stoppers are configured to limit the upstream axial motion of the reciprocating valve by contacting and blocking upstream axial motion of the upstream seal.

Inventive Concept 51. The mechanical circulatory assist device according to Inventive Concept 48, wherein the stent, when the stent and the coiled wire are in the radially-expanded configuration of the stent and the coiled wire, is shaped so as to define one or more downstream stoppers, which are configured to limit the downstream axial motion of the reciprocating valve when in the radially-expanded configuration of the reciprocating valve disposed within the stent.

Inventive Concept 52. The mechanical circulatory assist device according to any one of Inventive Concepts 1-14, wherein the reciprocating valve further includes an upstream seal that is annular when the reciprocating valve is in the radially-expanded configuration of the reciprocating valve.

Inventive Concept 53. The mechanical circulatory assist device according to Inventive Concept 52, wherein the reciprocating valve further includes a downstream seal that is annular when the reciprocating valve is in the radially-expanded configuration of the reciprocating valve.

Inventive Concept 54. The mechanical circulatory assist device according to any one of Inventive Concepts 1-14, further including openwork, which (a) includes a non-permanently-magnetized ferromagnetic metal, (b) is coupled to the coiled wire radially outward of the coiled wire when the stent and the coiled wire are in the radially-expanded configuration of the stent and the coiled wire, and (c) is configured to assume a radially-compressed configuration and a radially-expanded configuration.

Inventive Concept 55. The mechanical circulatory assist device according to Inventive Concept 54, wherein the non-permanently-magnetized ferromagnetic metal includes soft iron.

Inventive Concept 56. The mechanical circulatory assist device according to Inventive Concept 54, wherein the openwork includes a plurality of elongate metal rods.

Inventive Concept 57. The mechanical circulatory assist device according to any one of Inventive Concepts 1-14, wherein the stent includes a non-permanently-magnetized ferromagnetic metal.

Inventive Concept 58. The mechanical circulatory assist device according to Inventive Concept 57, wherein the non-permanently-magnetized ferromagnetic metal includes soft iron.

Inventive Concept 59. The mechanical circulatory assist device according to Inventive Concept 57, wherein the coiled wire is wound around the stent inside the stent.

Inventive Concept 60. A mechanical circulatory assist system including the mechanical circulatory assist device according to any one of Inventive Concepts 1-14, the mechanical circulatory assist system further including first and second delivery sheath longitudinal segments,
wherein the stent and the coiled wire are removably disposed in the first delivery sheath longitudinal segment with the stent and the coiled wire in the radially-compressed configuration of the stent and the coiled wire, and
wherein the reciprocating valve is removably disposed in the second delivery sheath longitudinal segment in the radially-compressed configuration of the reciprocating valve.

Inventive Concept 61. The mechanical circulatory assist system according to Inventive Concept 60, including a delivery sheath that includes the first and the second delivery sheath longitudinal segments.

Inventive Concept 62. The mechanical circulatory assist system according to Inventive Concept 60, including first and second delivery sheaths that include the first and the second delivery sheath longitudinal segments, respectively.

Inventive Concept 63. The mechanical circulatory assist system according to Inventive Concept 60, wherein the first delivery sheath longitudinal segment has an outer diameter of no more than 30 French, and wherein the second delivery sheath longitudinal segment has an outer diameter of no more than 30 French.

There is further provided, in accordance with an Inventive Concept 64 of the present invention, a method including:
delivering, to a location in a cardiovascular system of a subject, a mechanical circulatory assist device while a stent and a coiled wire of the mechanical circulatory assist device are in a radially-compressed configuration and a reciprocating valve of the mechanical circulatory assist device is in a radially-compressed configuration, wherein the coiled wire is wound around the stent inside, outside, or partially inside and partially outside the stent, and is configured to generate a magnetic field when current flows through the coiled wire when the stent and the coiled wire are in a radially-expanded configuration of the stent and the coiled wire; and
transitioning (a) the stent and the coiled wire to the radially-expanded configuration of the stent and the coiled wire, and (b) the reciprocating valve to a radially-expanded configuration of the reciprocating valve,
wherein the reciprocating valve includes (i) a housing; (ii) one or more leaflets, coupled to the housing; and (iii) one or more permanent magnets, which are coupled to the housing, and are arranged to interact with the magnetic field generated by the coiled wire, so as to axially move the reciprocating valve with respect to the stent when the reciprocating valve is in the radially-expanded configuration of the reciprocating valve disposed within the stent when the stent and the coiled wire are in the radially-expanded configuration of the stent and the coiled wire, and
wherein the reciprocating valve is configured such that:
upstream axial motion of the reciprocating valve causes the one or more leaflets to be in an open state in which the one or more leaflets allow blood flow through the reciprocating valve, and
downstream axial motion of the reciprocating valve causes the one or more leaflets to be in a closed state in which the one or more leaflets inhibit blood flow through the reciprocating valve.

Inventive Concept 65. The method according to Inventive Concept 64, wherein delivering the mechanical circulatory assist device to the cardiovascular system includes delivering the mechanical circulatory assist device to a blood vessel of the cardiovascular system downstream of a native aortic valve of a heart.

Inventive Concept 66. The method according to Inventive Concept 65, wherein transitioning includes transitioning the stent and the coiled wire to the radially-expanded configuration of the stent and the coiled wire such that the stent anchors the mechanical circulatory assist device to a wall of the blood vessel.

Inventive Concept 67. The method according to Inventive Concept 65, delivering the mechanical circulatory assist device to the blood vessel includes delivering the mechanical circulatory assist device to an aorta.

Inventive Concept 68. The method according to Inventive Concept 64, wherein delivering the mechanical circulatory assist device to the cardiovascular system includes delivering the mechanical circulatory assist device to a mitral valve of the cardiovascular system.

Inventive Concept 69. The method according to Inventive Concept 64, wherein delivering and transitioning include:

delivering the stent to the location in the cardiovascular system while the stent and the coiled wire are in the radially-compressed configuration of the stent and the coiled wire;

thereafter, transitioning the stent and the coiled wire to the radially-expanded configuration of the stent and the coiled wire;

thereafter, delivering the reciprocating valve into the stent at the location in the cardiovascular system while the reciprocating valve is in the radially-compressed configuration of the reciprocating valve; and thereafter, transitioning the reciprocating valve to the radially-expanded configuration of the reciprocating valve within the stent.

Inventive Concept 70. The method according to Inventive Concept 64, further including subjecting the coiled wire to a time-varying magnetic field generated outside a body of the subject when the stent and the coiled wire are in the radially-expanded configuration of the stent and the coiled wire, so as to electromagnetically induce the current in the coiled wire.

Inventive Concept 71. The method according to Inventive Concept 70, wherein subjecting the coiled wire to the time-varying magnetic field includes activating an external unit located outside the subject's body such that external-unit control circuitry of the external unit drives an external coil of the external unit to generate the time-varying magnetic field.

Inventive Concept 72. The method according to Inventive Concept 64, wherein delivering the mechanical circulatory assist device includes delivering the mechanical circulatory assist device while the stent and the coiled wire are removably disposed in a first delivery sheath longitudinal segment with the stent and the coiled wire in the radially-compressed configuration of the stent and the coiled wire, and the reciprocating valve is removably disposed in a second delivery sheath longitudinal segment in the radially-compressed configuration of the reciprocating valve.

Inventive Concept 73. The method according to Inventive Concept 72, wherein delivering the mechanical circulatory assist device includes delivering the mechanical circulatory assist device in a delivery sheath that includes the first and the second delivery sheath longitudinal segments.

Inventive Concept 74. The method according to Inventive Concept 72, wherein delivering the mechanical circulatory assist device includes delivering the mechanical circulatory assist device in first and second delivery sheaths that include the first and the second delivery sheath longitudinal segments, respectively.

There is still further provided, in accordance with an Inventive Concept 75 of the present invention, a mechanical circulatory assist system including:

(a) mechanical circulatory assist device configured to be deployed at a mitral valve of a cardiovascular system of a subject, the mechanical circulatory assist device including:
(i) a stent, which is configured to assume a radially-compressed configuration and a radially-expanded configuration; and
(ii) a reciprocating valve, which is configured to assume radially-compressed and radially-expanded configurations, and which includes a housing and one or more leaflets, coupled to the housing, wherein the reciprocating valve is configured to be axially moveable with respect to the stent when the reciprocating valve is in the radially-expanded configuration of the reciprocating valve disposed within the stent when the stent is in the radially-expanded configuration of the stent, wherein the reciprocating valve is configured such that:
upstream axial motion of the reciprocating valve causes the one or more leaflets to be in an open state in which the one or more leaflets allow blood flow through the reciprocating valve, and
downstream axial motion of the reciprocating valve causes the one or more leaflets to be in a closed state in which the one or more leaflets inhibit blood flow through the reciprocating valve; and (b) a sensor configured to sense at least one physiological parameter correlated with a cardiac cycle of the subject, wherein the mechanical circulatory assist system is configured to activate motion of the reciprocating valve only in a plurality of strokes during diastole of each cardiac cycle, as detected using the sensor, wherein each of the strokes includes the upstream axial motion and the downstream axial motion of the reciprocating valve.

Inventive Concept 76. The mechanical circulatory assist system according to Inventive Concept 75, wherein the at least one physiological parameter includes a left ventricular pressure.

Inventive Concept 77. The mechanical circulatory assist system according to Inventive Concept 75, wherein the at least one physiological parameter includes a feature of an electrocardiogram.

Inventive Concept 78. The mechanical circulatory assist system according to Inventive Concept 75, wherein the reciprocating valve is configured to be inserted into the stent when the stent is in the radially-expanded configuration of the stent and the reciprocating valve is in the radially-compressed configuration of the reciprocating valve.

There is additionally provided, in accordance with an Inventive Concept 79 of the present invention, an implantable device configured to be deployed in a body lumen of a subject, the implantable device including:

(a) a stent;

(b) a coiled wire, which is wound around the stent inside, outside, or partially inside and partially outside the stent, wherein the stent and the coiled wire are configured to assume a radially-compressed configuration and a radially-expanded configuration, wherein the coiled wire is configured to generate a magnetic field when current flows through the coiled wire when the stent and the coiled wire are in the radially-expanded configuration of the stent and the coiled wire; and (c) an inner component, which is configured to assume radially-compressed and radially-expanded configurations, and which includes:
(i) a housing; and
(ii) one or more permanent magnets, which are coupled to the housing, and are arranged to interact with the magnetic field generated by the coiled wire, so as to axially move the inner component with respect to the stent when the inner component is in the radially-expanded configuration of the inner component disposed within the stent when the stent and the coiled wire are in the radially-expanded configuration of the stent and the coiled wire.

Inventive Concept 80. The implantable device according to Inventive Concept 79, wherein the body lumen is a blood vessel, and wherein the implantable device is configured to be deployed in the blood vessel.

Inventive Concept 81. A system including the implantable device according to Inventive Concept 79, the system further including first and second delivery sheath longitudinal segments, wherein the stent and the coiled wire are removably disposed in the first delivery sheath longitudinal segment with the stent and the coiled wire in the radially-compressed configuration of the stent and the coiled wire, and wherein the inner component is removably disposed in the second delivery sheath longitudinal segment in the radially-compressed configuration of the inner component.

Inventive Concept 82. The system according to Inventive Concept 81, including a delivery sheath that includes the first and the second delivery sheath longitudinal segments.

Inventive Concept 83. The system according to Inventive Concept 81, including first and second delivery sheaths that include the first and the second delivery sheath longitudinal segments, respectively.

Inventive Concept 84. The system according to Inventive Concept 81, wherein the first delivery sheath longitudinal segment has an outer diameter of no more than 30 French, and wherein the second delivery sheath longitudinal segment has an outer diameter of no more than 30 French.

The present invention will be more fully understood from the following detailed description of applications thereof, taken together with the drawings, in which:

BRIEF DESCRIPTION OF THE DRAWINGS

FIGS. 6A-E are schematic illustrations of representative phases of a reciprocating pattern of a reciprocating valve of the mechanical circulatory assist device of FIG. 1, in accordance with an application of the present invention;

FIGS. 8A-B are schematic illustrations of another mechanical circulatory assist device, in accordance with an application of the present invention;

FIG. 13 is a schematic illustration of another mechanical circulatory assist device implanted at a native mitral valve, in accordance with an application of the present invention.

DETAILED DESCRIPTION OF APPLICATIONS

Figure 1:
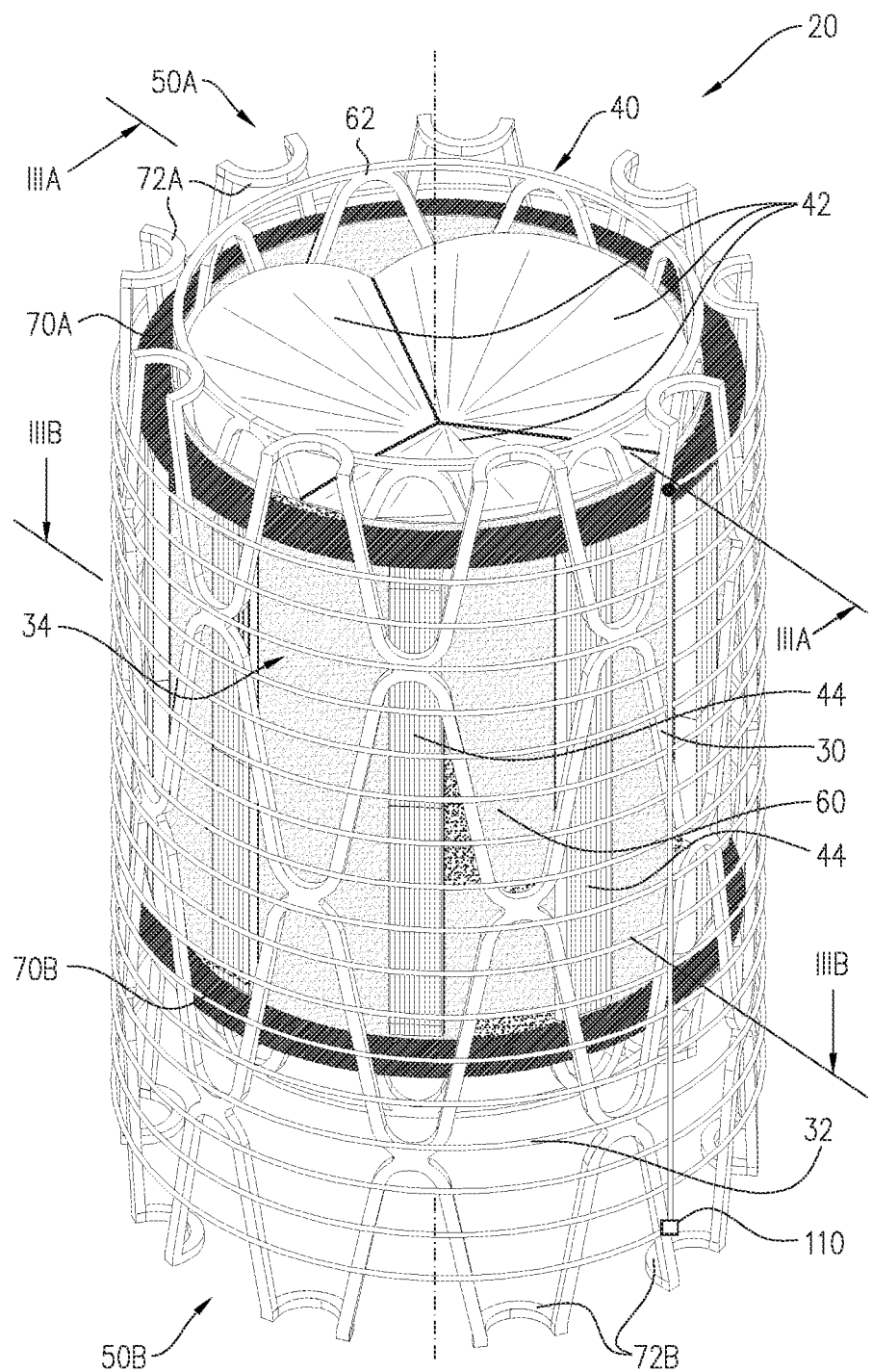
FIG. 1 is a schematic illustration of a mechanical circulatory assist device configured to be deployed in a cardiovascular system of a subject, in accordance with an application of the present invention.
Figure 2:
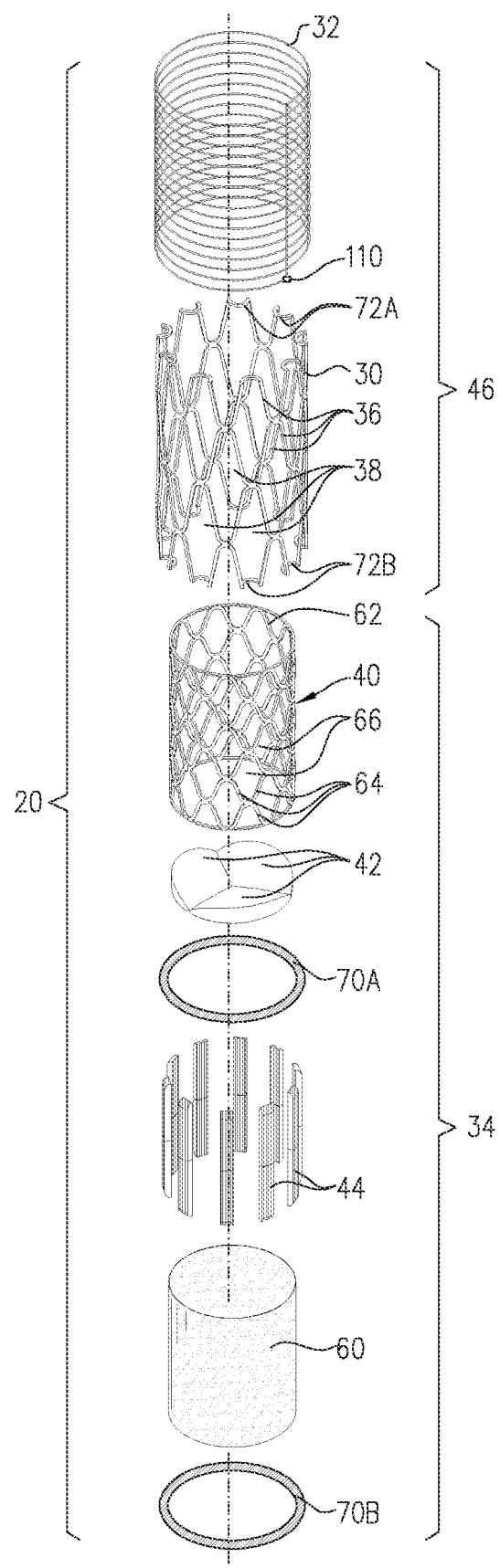
FIG. 2 is a schematic exploded view of the mechanical circulatory assist device of FIG. 1 showing elements of the device, in accordance with an application of the present invention.
Figure 3A:
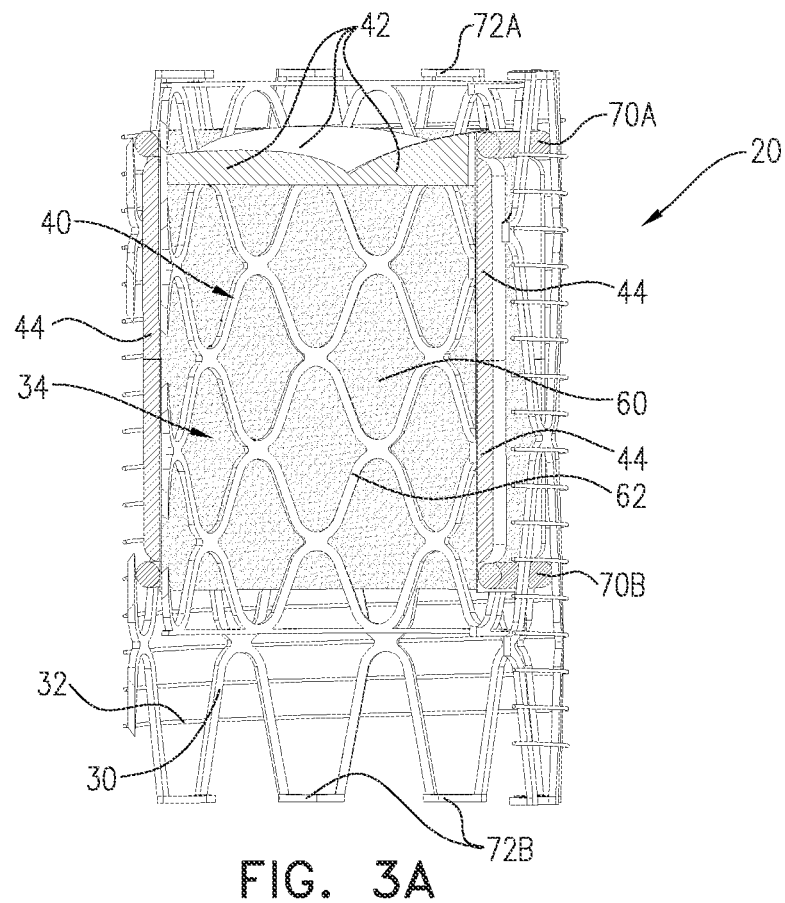
FIGS. 3A and 3B are schematic cross-sectional views of the mechanical circulatory assist device of FIG. 1 taken along lines IIIA-IIIA and IIIB-IIIB of FIG. 1, respectively, in accordance with an application of the present invention.
Figure 3B:
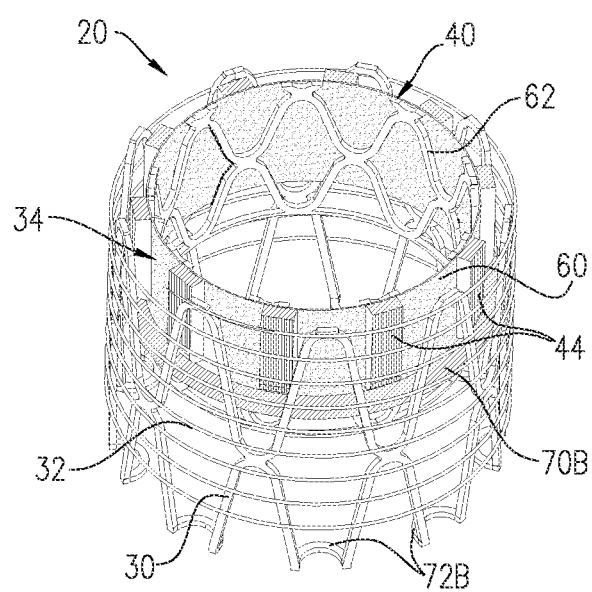

Reference is made to FIG. 1, which is a schematic illustration of a mechanical circulatory assist device 20 configured to be deployed in a cardiovascular system of a subject, in accordance with an application of the present invention. Reference is also made to FIG. 2, which is a schematic exploded view of mechanical circulatory assist device 20 showing elements of the device, in accordance with an application of the present invention. Reference is further made to FIGS. 3A and 3B, which are schematic cross-sectional views of mechanical circulatory assist device 20 taken along lines IIIA-IIIA and IIIB-IIIB of FIG. 1, respectively, in accordance with an application of the present invention.

Figure 5A:
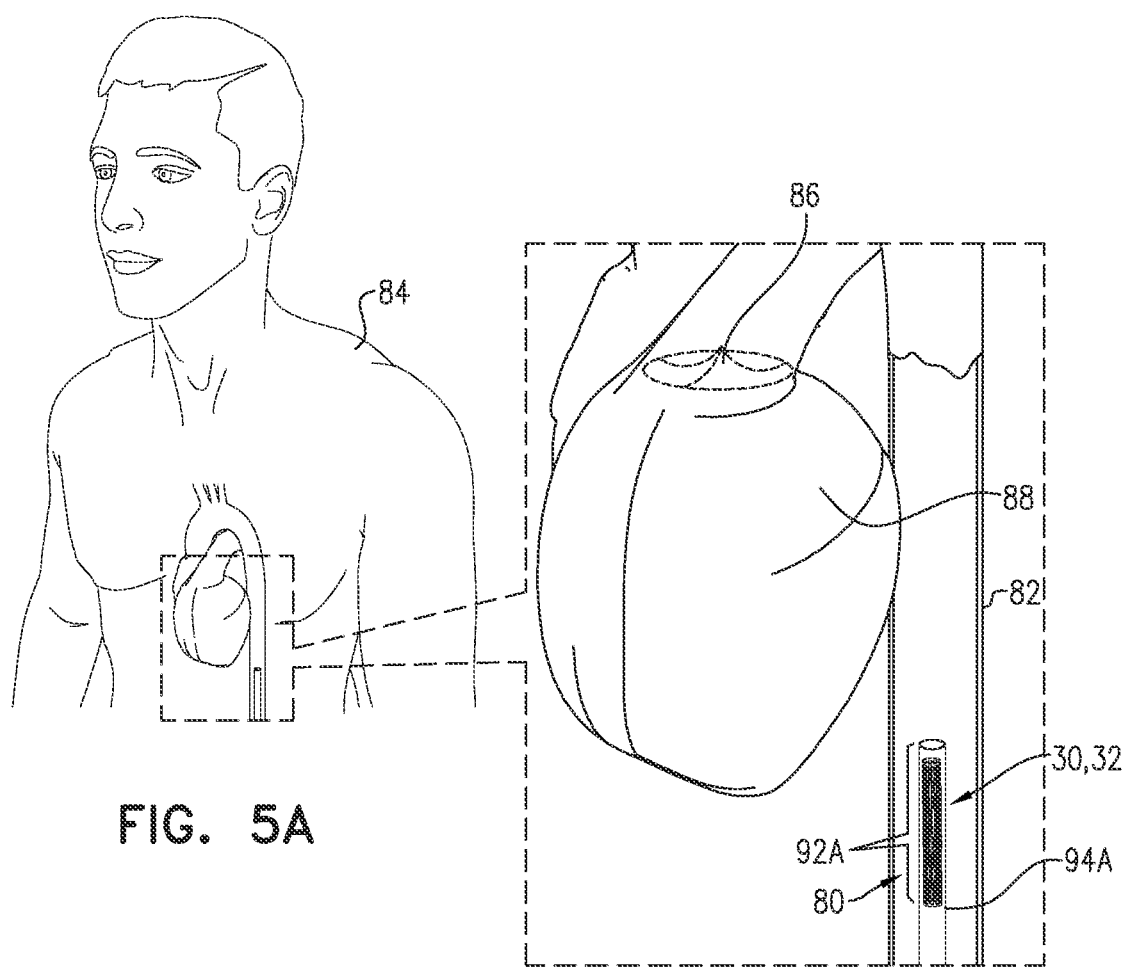
FIGS. 5A-D are schematic illustrations of a method using the mechanical circulatory assist device of FIG. 1, in accordance with an application of the present invention.

Mechanical circulatory assist device 20 comprises a stent 30, a coiled wire 32, and a reciprocating valve 34. Stent 30 and coiled wire 32 are configured to assume a radially-compressed configuration of stent 30 and coiled wire 32, such as shown in FIG. 5A, described hereinbelow, and a radially-expanded configuration of stent 30 and coiled wire 32, such as shown in FIG. 1 and several of the other figures. For some applications in which mechanical circulatory assist device 20 is configured to be deployed in a blood vessel of the cardiovascular system, stent 30 is configured to anchor mechanical circulatory assist device 20 to the wall of the blood vessel, when stent 30 and coiled wire 32 are in the radially-expanded configuration of stent 30 and coiled wire 32, such as described hereinbelow with reference to FIG. 5B. Typically, when stent 30 and coiled wire 32 are in the radially-expanded configuration of stent 30 and coiled wire 32, stent 30 is generally tubular, such as generally cylindrical, as shown in the figures. Typically, stent 30 comprises interconnected stent struts 36 arranged so as to define interconnected stent cells 38 (labeled in FIG. 2).

Coiled wire 32 is wound around stent 30 inside stent 30 (such as described hereinbelow with reference to FIG. 12), outside stent 30 (such as shown in the figures other than FIG. 12), or partially inside and partially outside stent 30 (configuration not shown). Coiled wire 32 is configured to generate a magnetic field when current flows through coiled wire 32 when stent 30 and coiled wire 32 are in the radially-expanded configuration of stent 30 and coiled wire 32.

For some applications, coiled wire 32 is shaped so as to define 10-100 wire turns. Alternatively or additionally, for some applications, coiled wire 32 is shaped so as to have a pitch of 0.2-2 mm.

Stent 30 and coiled wire 32 are typically elements of an assembly 46, which is cylindrical when stent 30 and coiled wire 32 are in the radially-expanded configuration of stent 30 and coiled wire 32. Assembly 46 is configured to assume a radially-compressed configuration when stent 30 and coiled wire 32 are in the radially-compressed configuration thereof.

Figure 5B:
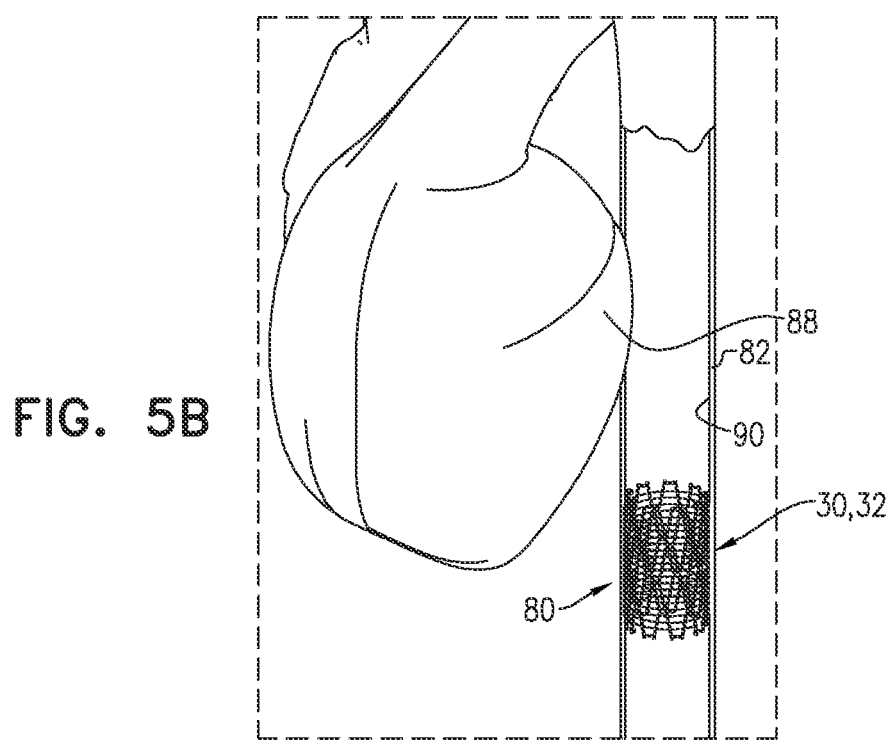
Figure 5C:
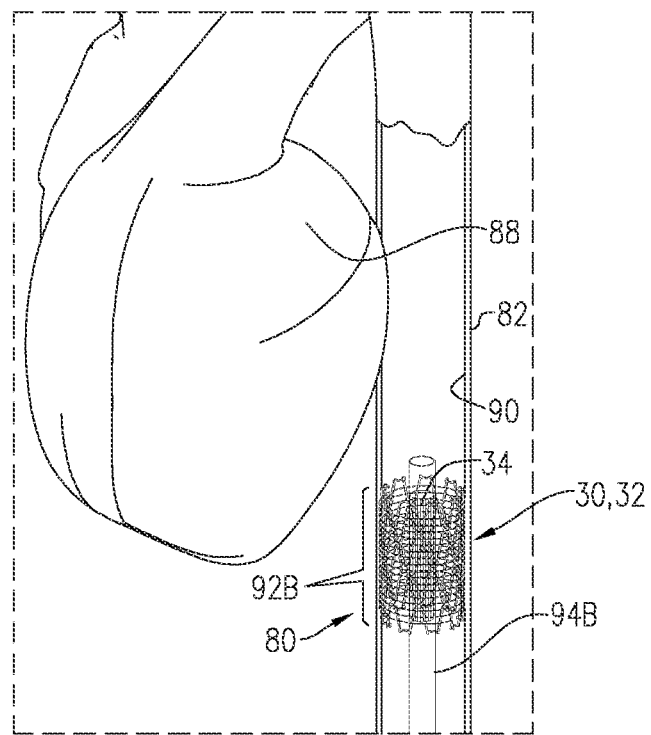

Reciprocating valve 34 is configured to assume a radially-compressed configuration, such as shown in FIG. 5C, described hereinbelow, and a radially-expanded configuration, such as shown in FIG. 1 and several of the other figures. Reciprocating valve 34 comprises a housing 40, one or more leaflets 42 coupled to housing 40, and one or more permanent magnets 44. The one or more permanent magnets 44 are coupled to housing 40, and are arranged to interact with the magnetic field generated by coiled wire 32, so as to axially move (typically axially slide) reciprocating valve 34 with respect to stent 30 when reciprocating valve 34 is in the radially-expanded configuration of reciprocating valve 34 disposed within stent 30 when stent 30 and coiled wire 32 are in the radially-expanded configuration of stent 30 and coiled wire 32.

For some applications, mechanical circulatory assist device 20 is configured to provide a relative high force for downstream pumping of blood, such as at least 150 gram-force (and typically no more than 200 gram-force). Typically, reciprocating valve 34 comprises 10-20 permanent magnets 44. (If fewer, larger magnets were instead provided, it would be more difficult to crimp reciprocating valve 34 into a delivery catheter.) Typically, the one or more permanent magnets comprise one or more alloys of iron, nickel, cobalt, one or more rare-earth metals, and/or neodymium.

As described in more detail hereinbelow with reference to FIGS. 6A-E, reciprocating valve 34 is configured such that:
upstream axial motion of reciprocating valve 34 causes the one or more leaflets 42 to be in an open state in which the one or more leaflets 42 allow blood flow through reciprocating valve 34, and
downstream axial motion of reciprocating valve 34 causes the one or more leaflets 42 to be in a closed state in which the one or more leaflets 42 inhibit blood flow through reciprocating valve 34.

As described in more detail hereinbelow with reference to FIGS. 6A-E, reciprocating valve 34 typically affects blood flow in the cardiovascular system (e.g., the blood vessel) by reciprocation between:
the closed state of the one or more leaflets 42 in which downstream axial motion of reciprocating valve 34 pushes blood downstream in the cardiovascular system (e.g., the blood vessel), thereby assisting functioning of the heart, and
the open state of the one or more leaflets 42 in which upstream axial motion of reciprocating valve 34 has minimal effect on blood flow.

For some applications, mechanical circulatory assist device 20 is configured such that reciprocating valve 34 moves 10-20 mm with respect to stent 30 in each direction (downstream and upstream) during an entire cycle of a reciprocating pattern, such as 12-18 mm, e.g., 15 mm.

For some applications, such as for treating heart failure, mechanical circulatory assist device 20 is configured to increase blood flow by 5-10 ml per second, which typically increases blood flow by about 10%-20%. For some applications, each stroke of reciprocating valve 34 may pump 4-5 ml, such that reciprocating valve 34 pumps 4-25 ml per second if the reciprocating valve reciprocates at a frequency of 1-5 Hz, respectively. (For example, the one or more leaflets 42 may have an aggregate surface area of about 3 cm2, such that if reciprocating valve 34 moves 15 mm with respect to stent 30 in each direction (downstream and upstream) during an entire cycle of a reciprocating pattern, each stroke would pump 4.5 ml.)

Figure 4:
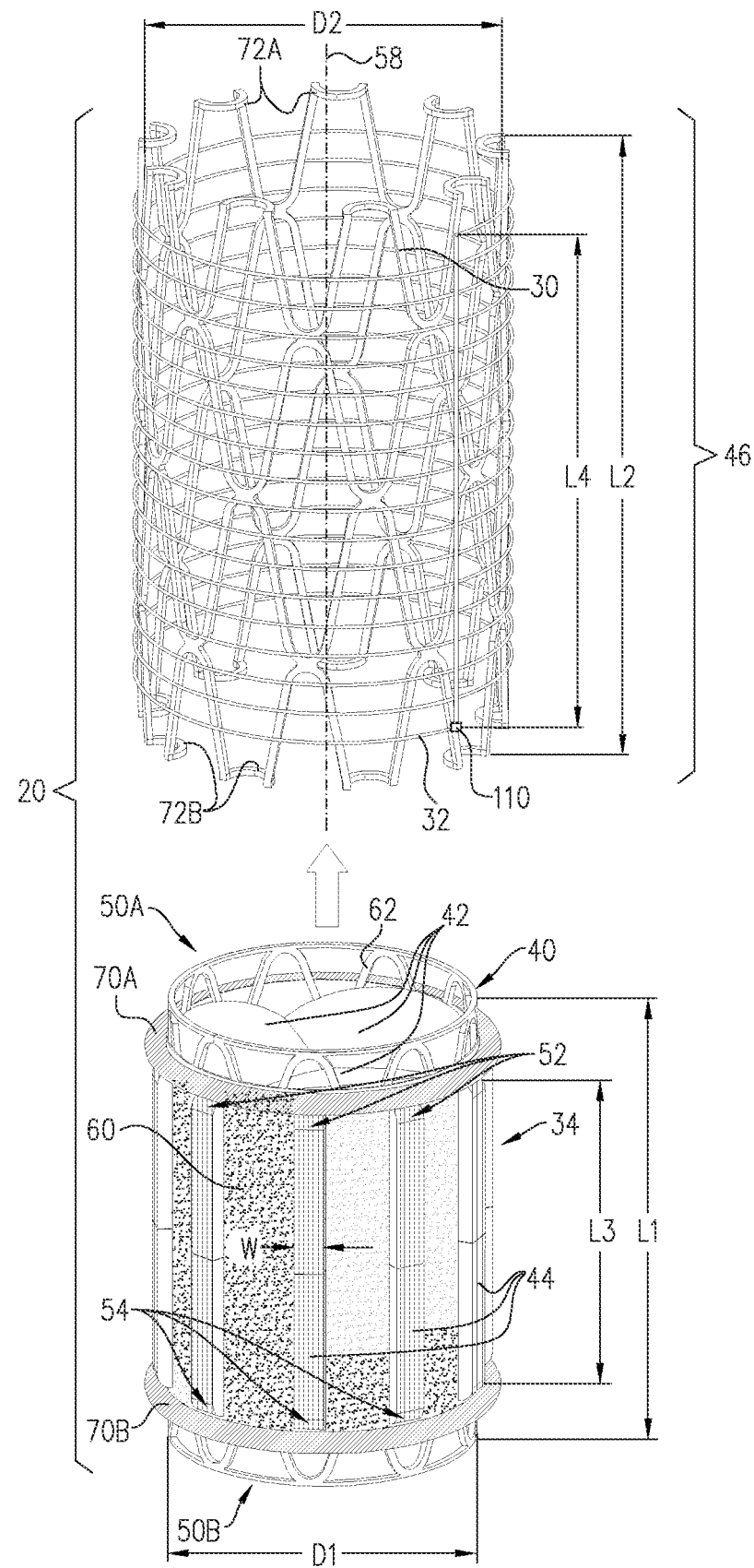
FIG. 4 is a schematic illustration of the mechanical circulatory assist device of FIG. 1 before insertion of a reciprocating valve thereof into a stent thereof, in accordance with an application of the present invention.

Reference is now made to FIG. 4, which is a schematic illustration of mechanical circulatory assist device 20 before insertion of reciprocating valve 34 into stent 30, in accordance with an application of the present invention. In some applications of the present invention, reciprocating valve 34 and stent 30 are two separate pieces that are configured to be assembled together in situ during a deployment procedure, such as described hereinbelow with reference to FIGS. 5A-D. For some of these applications, reciprocating valve 34 is configured to be inserted into stent 30 when stent 30 and coiled wire 32 are in the radially-expanded configuration of stent 30 and coiled wire 32 and reciprocating valve 34 is in the radially-compressed configuration of reciprocating valve 34. For clarity of illustration only, reciprocating valve 34 is shown in FIG. 4 in the radially-expanded configuration of reciprocating valve 34; in practice in this configuration, reciprocating valve 34 is actually inserted into stent 30 while reciprocating valve 34 is in the radially-compressed configuration of reciprocating valve 34, such as described hereinbelow with reference to FIGS. 5C-D.

In some applications of the present invention, reciprocating valve 34 and assembly 46 are two separate pieces that are configured to be assembled together in situ during a deployment procedure, such as described hereinbelow with reference to FIGS. 5A-D. For some of these applications, reciprocating valve 34 is configured to be inserted into assembly 46 when assembly 46 is in a radially-expanded configuration of assembly 46 and reciprocating valve 34 is in the radially-compressed configuration of reciprocating valve 34.

Reference is still made to FIG. 4 and is again made to FIGS. 1-3B. Stent 30 has upstream and downstream ends 50A and 50B. For some applications, the one or more permanent magnets 44 are elongate. For some applications, the one or more permanent magnets 44 have one or more respective pairs of opposite first poles 52 and second poles 54 (labeled in FIG. 4). The one or more permanent magnets 44 are oriented such that first poles 52 are closer to upstream end 50A of housing 40 than second poles 54 are to upstream end 50A of housing 40. Typically, the one or more permanent magnets 44 are oriented parallel to a longitudinal axis of reciprocating valve 34 when reciprocating valve 34 is in the radially-expanded configuration of reciprocating valve 34.

For some applications, the one or more leaflets 42 comprise animal tissue, e.g., porcine pericardium, which is typically a relatively thick membrane (e.g., on the order of 1-2 mm). Alternatively, the one or more leaflets 42 comprise a biocompatible synthetic material such as polyurethane or polyethylene.

For some applications, reciprocating valve 34 comprises two or more leaflets 42, such as 2-6 leaflets 42, e.g., exactly three leaflets 42, as shown.

Reference is again made to FIG. 4. The following elements of mechanical circulatory assist device 20 have the following dimensions:
housing 40 has a housing length L1 and a housing outer diameter D1, when reciprocating valve 34 is in the radially-expanded configuration of reciprocating valve 34,
stent 30 has a stent length L2 and a stent inner diameter D2, when stent 30 and coiled wire 32 are in the radially-expanded configuration of stent 30 and coiled wire 32,
the one or more permanent magnets 44 have an average magnet length L3, and
coiled wire 32 has a coil axial length L4, measured along an axis 58 of stent 30 when stent 30 and coiled wire 32 are in the radially-expanded configuration of stent 30 and coiled wire 32.

Reference is still made to FIG. 4. For some applications, when reciprocating valve 34 is in the radially-expanded configuration of reciprocating valve 34 and stent 30 and coiled wire 32 are in the radially-expanded configuration of stent 30 and coiled wire 32:
the average magnet length L3 is 70%-100%, such as between 80%-95%, of the housing length L1, the average magnet length L3 is 60%-100%, such as 70%-95%, of the coil axial length L4, the housing length L1 is 50%-90% of the stent length L2, the housing outer diameter D1 is (a) 80%-95%, such as 82%-90%, of the stent inner diameter D2, and/or (b) 3-5 mm less than the stent inner diameter D2, the coil axial length L4 is 50%-90%, such as 60%-85%, of the stent length L2, and/or the coil axial length L4 is 50%-100%, such as 65%-90%, of the housing length L1.

Alternatively or additionally, for some applications, when reciprocating valve 34 is in the radially-expanded configuration of reciprocating valve 34 and stent 30 and coiled wire 32 are in the radially-expanded configuration of stent 30 and coiled wire 32:

the housing length L1 is 10-30 mm, the stent length L2 is 20-35 mm, the average magnet length L3 is 10-25 mm, the coil axial length L4 is 15-25 mm, such as 20 mm, the housing outer diameter D1 is 15-30 mm, e.g., 20-30 mm, the stent inner diameter D2 is 15-30 mm, e.g., 20-30 mm, and/or stent 30 has an outer diameter of 15-30 mm, e.g., 20-30 mm.

Reference is again made to FIGS. 1-4. For some applications, housing 40 is cylindrical when in the radially-expanded configuration of reciprocating valve 34. The cylindrical housing may be elliptical (e.g., circular, as shown). Alternatively, housing 40 has another shape.

Reference is again made to FIG. 4. When reciprocating valve 34 is in the radially-expanded configuration of reciprocating valve 34, the one or more permanent magnets 44 have one or more respective widths W, measured around a circumference of housing 40. For some applications:

a sum of the one or more widths W subtends 90-150 degrees, such as 105-135 degrees, of a circumference of housing 40, and/or each of widths W equals 1-3 mm, such as 1.5-2.5 mm, e.g., 2 mm.

Reference is again made to FIGS. 1-4. For some applications, reciprocating valve 34 further comprises a blood-proof membrane 60 that is tubular when reciprocating valve 34 is in the radially-expanded configuration of reciprocating valve 34. Blood-proof membrane 60 may be coupled to an outer surface of housing 40 (as shown) or an inner surface of housing 40 (configuration not shown), e.g., by stitching, welding, and/or gluing. In either case, the one or more permanent magnets 44 are typically disposed radially outward from blood-proof membrane 60, typically in contact with blood-proof membrane 60. Blood-proof membrane 60 may help prevent turbulence between blood and the one or more permanent magnets 44 and help prevent clots. Optionally, blood-proof membrane 60 comprises a polymer (such as polyurethane), latex, silicone, or a fabric.

For some applications, stent 30 is an outer stent 30, and housing 40 comprises a housing stent 62 comprising interconnected stent struts 64 arranged so as to define interconnected stent cells 66 (labeled in FIG. 2). Typically, each of magnets 44 is coupled to housing stent 62 at exactly one axial location along housing stent 62, in order to allow housing stent 62 to elongate during crimping of the housing stent into a delivery catheter.

For some applications, reciprocating valve 34 further comprises an upstream seal 70A that is annular when reciprocating valve 34 is in the radially-expanded configuration of reciprocating valve 34. Upstream seal 70A may help prevent blood flow between housing 40 and stent 30, such as between blood-proof membrane 60 and stent 30 in applications in which blood-proof membrane 60 is provided. For example, upstream seal 70A may comprise an elastomer.

Alternatively or additionally, for some applications, reciprocating valve 34 further comprises a downstream seal 70B that is annular when reciprocating valve 34 is in the radially-expanded configuration of reciprocating valve 34. Downstream seal 70B may help prevent blood flow between housing 40 and stent 30, such as between blood-proof membrane 60 and stent 30 in applications in which blood-proof membrane 60 is provided. For example, downstream seal 70B may comprise an elastomer.

For some applications, when stent 30 and coiled wire 32 are in the radially-expanded configuration of stent 30 and coiled wire 32, stent 30 is shaped so as to define one or more upstream stoppers 72A, which are configured to limit the upstream axial motion of reciprocating valve 34 when in the radially-expanded configuration of reciprocating valve 34 disposed within stent 30. In other words, the one or more upstream stoppers 72A set a maximum for the upstream axial motion of reciprocating valve 34. For some of these applications, stent 30 comprises interconnected stent struts 36 arranged so as to define interconnected stent cells 38, and some of stent struts 36 are bent radially inward so as to define the one or more upstream stoppers 72A.

For some applications in which reciprocating valve 34 further comprises upstream seal 70A, as described above, the one or more upstream stoppers 72A are configured to limit the upstream axial motion of reciprocating valve 34 by contacting and blocking upstream axial motion of the upstream seal 70A.

For some applications, when stent 30 and coiled wire 32 are in the radially-expanded configuration of stent 30 and coiled wire 32, stent 30 is shaped so as to define one or more downstream stoppers 72B, which are configured to limit the downstream axial motion of reciprocating valve 34 when in the radially-expanded configuration of reciprocating valve 34 disposed within stent 30. In other words, the one or more downstream stoppers 72B set a maximum for the downstream axial motion of reciprocating valve 34. For some of these applications, stent 30 comprises interconnected stent struts 36 arranged so as to define interconnected stent cells 38, and some of stent struts 36 are bent radially inward so as to define the one or more downstream stoppers 72B.

For some applications in which reciprocating valve 34 further comprises downstream seal 70B, as described above, the one or more downstream stoppers 72B are configured to limit the downstream axial motion of reciprocating valve 34 by contacting and blocking downstream axial motion of the downstream seal 70B.

Reference is now made to FIGS. 5A-D, which are schematic illustrations of a method using mechanical circulatory assist device 20, in accordance with an application of the present invention. The method may also be used with mechanical circulatory assist device 120, described hereinbelow with reference to FIGS. 8A-B, mutatis mutandis.

As shown in FIGS. 5A and 5C, mechanical circulatory assist device 20 is delivered to a location 80 in a blood vessel 82 of a subject 84 (such as an aorta, as shown) downstream of a native aortic valve 86 of a heart 88 of subject 84, a while stent 30 and coiled wire 32 are in the radially-compressed configuration of stent 30 and coiled wire 32 and reciprocating valve 34 is in the radially-compressed configuration of reciprocating valve 34, respectively. (Typically, mechanical circulatory assist device 20 is not implanted too close to the aortic valve, such that the blood pressure stored in the aortic wall between the aortic valve and mechanical circulatory assist device 20 during systole is sufficient to provide blood flow to the coronary arteries during diastole. Alternatively, mechanical circulatory assist device 20 is implanted at an aortic valve.) Systole and diastole, as used herein, including in the claims and Inventive Concepts, mean ventricular systole and ventricular diastole, respectively.

For example, mechanical circulatory assist device 20 may be advanced in a delivery tool, e.g., one or more catheters, through a femoral artery in a retrograde direction and along the aorta until a desired location downstream of the native aortic valve is reached.

It is noted that FIGS. 5A-D show blood vessel 82 as the aorta and mechanical circulatory assist device 20 is shown in the aorta by way of illustration and not limitation. For some applications, mechanical circulatory assist device 20 is deployed in another blood vessel 82, e.g., a vena cava of the subject, or elsewhere in the cardiovascular system, such as at a mitral valve, such as described hereinbelow with reference to FIG. 13.

Figure 5D:
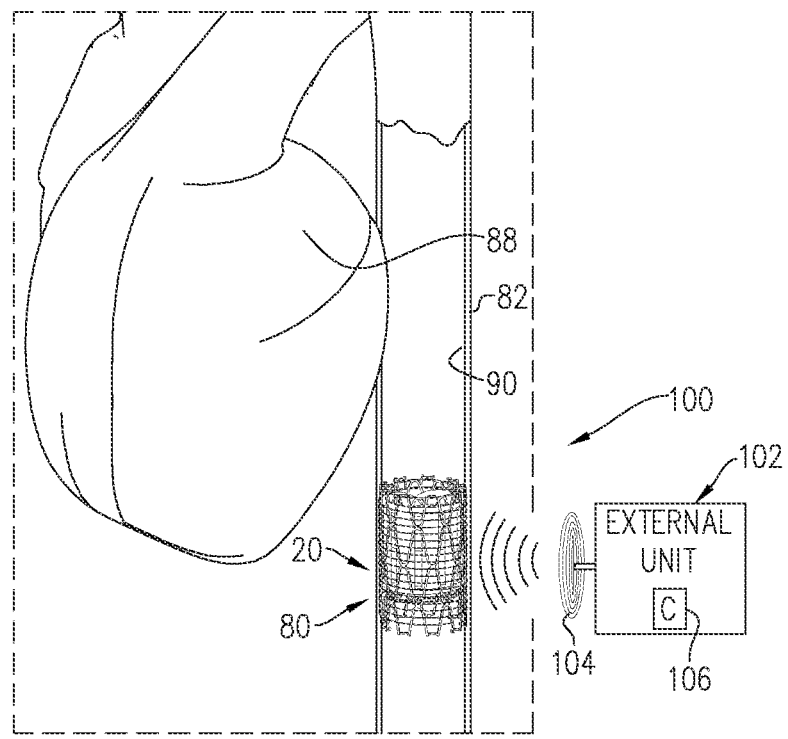

As shown in FIGS. 5B and 5D, the method further comprises transitioning (a) stent 30 and coiled wire 32 to the radially-expanded configuration of stent 30 and coiled wire 32 so as to anchor mechanical circulatory assist device 20 to a wall 90 of blood vessel 82, and (b) reciprocating valve 34 to the radially-expanded configuration of reciprocating valve 34. For some applications, stent 30 comprises a shape-memory material, such as Nitinol, such that stent 30 self-expands upon release from first delivery sheath longitudinal segment 92A, described hereinbelow. Alternatively or additionally, stent 30 is expanded using a balloon, as is known in the stent-deployment art (such as in the configuration described hereinbelow with reference to FIG. 12). Deployment of mechanical circulatory assist device 20 in the cardiovascular system (e.g., blood vessel 82) facilitates blood flow in the cardiovascular system, e.g., the blood vessel, such as described hereinbelow with reference to FIGS. 6A-E.

For some applications, wherein delivering and transitioning comprise:
- as shown in FIG. 5A, delivering stent 30 to location 80 in the cardiovascular system, e.g., blood vessel 82, while stent 30 and coiled wire 32 are in the radially-compressed configuration of stent 30 and coiled wire 32;
- thereafter, as shown in FIG. 5B, transitioning stent 30 and coiled wire 32 to the radially-expanded configuration of stent 30 and coiled wire 32 so as to anchor mechanical circulatory assist device 20 to wall 90 of blood vessel 82;
- thereafter, as shown in FIG. 5C, delivering reciprocating valve 34 into stent 30 at location 80 in the cardiovascular system, e.g., blood vessel 82, while reciprocating valve 34 is in the radially-compressed configuration of reciprocating valve 34; and
- thereafter, as shown in FIG. 5D, transitioning reciprocating valve 34 to the radially-expanded configuration of reciprocating valve 34 within stent 30.

For some applications, delivering mechanical circulatory assist device 20 comprises delivering mechanical circulatory assist device 20 while stent 30 and coiled wire 32 are removably disposed in a first delivery sheath longitudinal segment 92A in the radially-compressed configuration of stent 30 and coiled wire 32, as shown in FIG. 5A, and reciprocating valve 34 is removably disposed in a second delivery sheath longitudinal segment 92B in the radially-compressed configuration of reciprocating valve 34, as shown in FIG. 5C.

For some applications, such as shown in FIGS. 5A and 5C, delivering mechanical circulatory assist device 20 comprises delivering mechanical circulatory assist device 20 in first and second delivery sheaths 94A and 94B that include first and second delivery sheath longitudinal segments 92A and 92B, respectively. For other applications, delivering mechanical circulatory assist device 20 comprises delivering mechanical circulatory assist device 20 in a delivery sheath that includes first and second delivery sheath longitudinal segments 92A and 92B (configuration not shown).

For some applications, first delivery sheath longitudinal segment 92A has an outer diameter of no more than 30 French, such as 22-30 French, and/or second delivery sheath longitudinal segment 92B has an outer diameter of no more than 30 French, such as 22-30 French.

Reference is made to FIG. 5D. For some applications, coiled wire 32 is configured such that the current is electromagnetically induced in coiled wire 32 when coiled wire 32 is subjected to a time-varying magnetic field generated outside a body of subject 84 when stent 30 and coiled wire 32 are in the radially-expanded configuration of stent 30 and coiled wire 32 with stent 30 anchoring mechanical circulatory assist device 20 to wall 90 of blood vessel 82. For these applications, the method further comprises subjecting coiled wire 32 to a time-varying magnetic field generated outside the body of subject 84 when stent 30 and coiled wire 32 are in the radially-expanded configuration of stent 30 and coiled wire 32 with stent 30 anchoring mechanical circulatory assist device 20 to wall 90 of blood vessel 82, so as to electromagnetically induce the current in coiled wire 32.

Reference is still made to FIG. 5D. For some applications, a mechanical circulatory assist system 100 is provided that comprises mechanical circulatory assist device 20 and an external unit 102, which comprises:
- an external coil 104, which is configured to be placed outside the body of subject 84; and
- external-unit control circuitry 106, which is configured to drive external coil 104 to generate the time-varying magnetic field.

For these applications, subjecting coiled wire 32 to the time-varying magnetic field comprises activating external unit 102 located outside the body of subject 84 body such that external-unit control circuitry 106 drives external coil 104 to generate the time-varying magnetic field.

For some applications, external-unit control circuitry 106 is configured to drive external coil 104 to generate the time-varying magnetic field at a frequency of 5.6-14 MHz. Alternatively or additionally, for some applications, external-unit control circuitry 106 is configured to drive external coil 104 to generate the time-varying magnetic field to generate 5-12 V in coiled wire 32.

For some applications, external-unit control circuitry 106 is configured to drive external coil 104 to generate the time-varying magnetic field such that reciprocating valve 34 reciprocates at a frequency of 1-5 Hz, e.g., 2-5 Hz, such as 2-3 Hz, e.g., 2-4 Hz. This frequency is typically higher than that of an ordinary beating adult human heart. Reciprocation at a frequency of at least 2 Hz typically obviates any need to coordinate the timing of the strokes of reciprocating valve 34 with systole of the heart, and allows the use of smaller pump than might be necessary at a lower frequency.

For some applications, external-unit control circuitry 106 is configured to operate at a reciprocating frequency that is adjustable only by an external user interface.

For some applications, external-unit control circuitry 106 is configured to drive external coil 104 to generate the time-varying magnetic field such that reciprocating valve 34 pushes blood at the above-mentioned rates.

Typically, external-unit control circuitry 106 is not configured to drive external coil 104 to generate the time-varying magnetic field in coordination with a cardiac cycle of subject 84.

In applications in which mechanical circulatory assist device 20 is configured to be implanted in blood vessel 82, mechanical circulatory assist system 100 typically does not comprise any sensor of heart rate or cardiac cycle. For example, the reciprocating motion of reciprocating valve 34 (moving of reciprocating valve 34 upstream and downstream) is typically not dependent on the frequency of heart beats, and reciprocating valve 34 is typically not operated in a synchronous pattern with respect to the diastole and systole of the subject. Alternatively, mechanical circulatory assist system 100 comprises a sensor of the cardiac cycle, such as described hereinbelow with reference to FIG. 13.

Reference is now made to FIGS. 6A-E, which are schematic illustrations of representative phases of a reciprocating pattern of reciprocating valve 34 during a single of cycle of the reciprocating pattern, in accordance with an application of the present invention. FIG. 6A shows mechanical circulatory assist device 20 with reciprocating valve 34 at the beginning of the single cycle, and FIG. 6E shows mechanical circulatory assist device 20 with reciprocating valve 34 at the end of the single cycle, in the same position and state as at the beginning of the single cycle.

FIGS. 6A, 6B, and 6E show mechanical circulatory assist device 20 when the one or more leaflets 42 of reciprocating valve 34 are in the closed state, such that blood is inhibited from flowing through reciprocating valve 34. During the transition between the phases shown in FIGS. 6A and 6B, reciprocating valve 34 moves downstream while the one or more leaflets 42 are in the closed state, thereby pushing blood downstream in the cardiovascular system, e.g., blood vessel 82, during this portion of the cycle of the reciprocating pattern. Typically, the downstream motion of reciprocating valve 34 automatically transitions the one or more leaflets 42 to the closed state.

FIG. 6C shows mechanical circulatory assist device 20 after the one or more leaflets 42 have transitioned to the open state upon upstream axial motion of reciprocating valve 34, because of the pressure gradient across the one or more leaflets 42 created by the upstream motion of reciprocating valve 34. In this open state, the one or more leaflets 42 allow blood flow through reciprocating valve 34. During the transition between the phases shown in FIGS. 6C and 6E, reciprocating valve 34 moves upstream while the one or more leaflets 42 are in the open state, such that blood is allowed to flow through reciprocating valve 34, thereby allowing natural cardiac-driven downstream blood flow (e.g., during systole) through reciprocating valve 34 as reciprocating valve 34 moves upstream during this portion of the cycle of the reciprocating pattern.

It is noted that the blood flow symbolically shown in FIGS. 6C-E is not caused by reciprocating valve 34; when the one or more leaflets 42 are open, reciprocating valve 34 at most interferes only minimally with natural blood flow. In addition, as mentioned above, in configurations in which mechanical circulatory assist device 20 is configured to be implanted in blood vessel 82, reciprocating valve 34 is typically not operated in a synchronous pattern with respect to the diastole and systole of the subject. Therefore, when FIGS. 6C-E of the cycle of the reciprocating pattern happen to fall at least partially during diastole, there may be no or very little blood flow during a portion of the cycle of the reciprocating pattern that happens to fall during diastole.

Upon completion of last phase of the reciprocating pattern shown in FIG. 6E, the cycle repeats as reciprocating valve 34 again begins to move downstream in the cardiovascular system, e.g., blood vessel 82, at the phase of the reciprocating pattern shown in FIG. 6A.

Reference is made to FIGS. 1-6E. For some applications, mechanical circulatory assist device 20 is configured such that all implanted elements of mechanical circulatory assist device 20 other than stent 30 and coiled wire 32 may be decoupled from stent 30 after implantation and explanted, leaving stent 30 and coiled wire 32 implanted. Optionally, these explanted elements may be replaced with other similar elements by introducing these other similar elements into the body and coupling them to stent 30.

Reference is again made to FIGS. 1, 2, and 4. For some applications, mechanical circulatory assist device 20 further comprises a circuit 110 in electrical communication with the two ends of coiled wire 32. Typically, mechanical circulatory assist device 20, including circuit 110, does not comprise any active electronic components.

Figure 7:
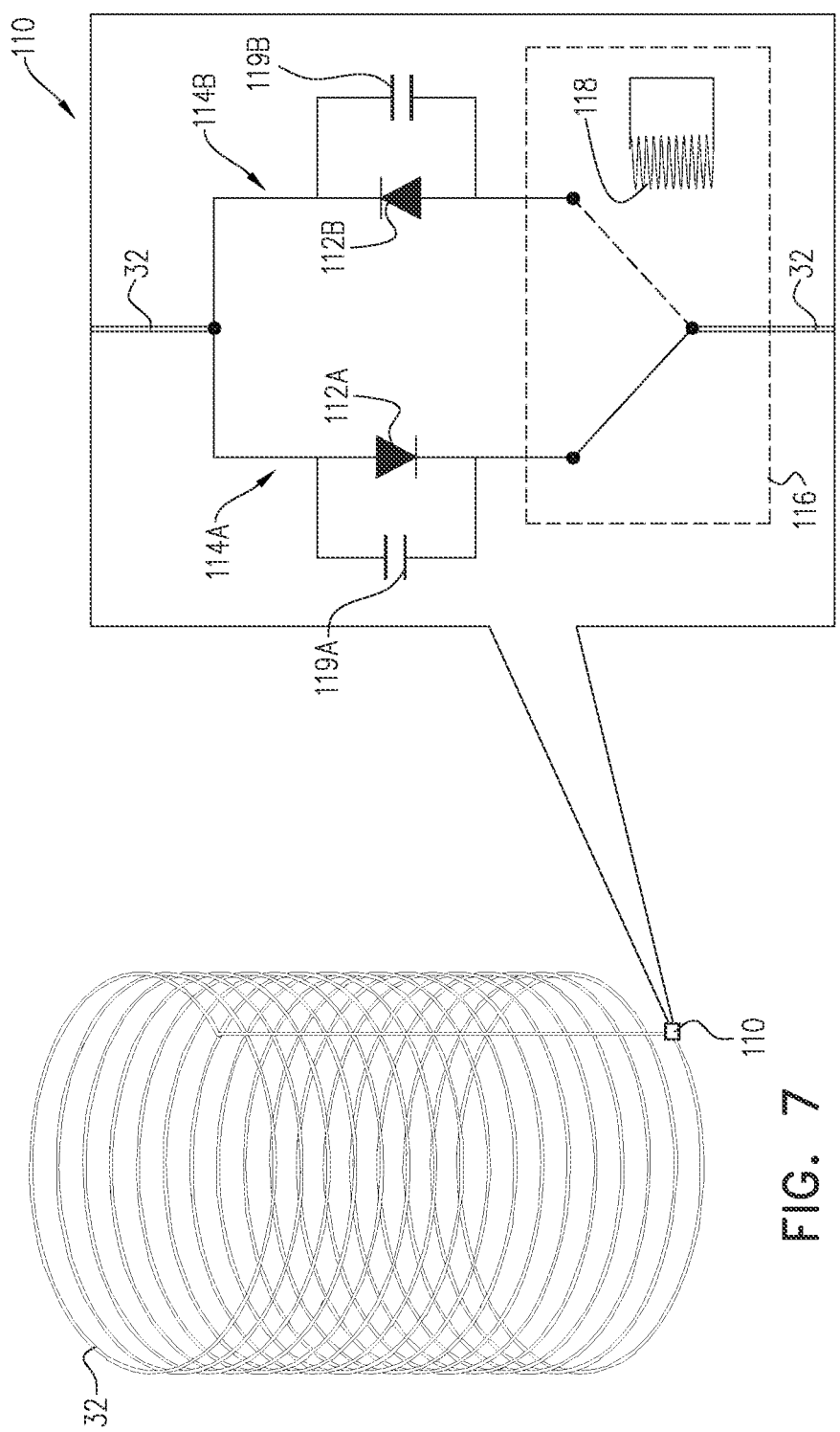
FIG. 7 is a schematic illustration of a coiled wire and a circuit of the mechanical circulatory assist device of FIG. 1, in accordance with an application of the present invention.

Reference is now made to FIG. 7, which is a schematic illustration of coiled wire 32 and circuit 110 of mechanical circulatory assist device 20, in accordance with an application of the present invention. In this configuration, mechanical circulatory assist device 20 further comprises:

first and second passive diodes 112A and 112B, which are
(a) arranged in parallel along respective first and second branches 114A and 114B of circuit 110, and (b) configured to rectify the current in the respective branches in respective opposite first and second directions; and a switch 116 (e.g., a flip-flop switch), which is arranged to selectively assume first and second states, in which the switch electrically couples only first branch 114A and only second branch 114B, respectively, to coiled wire 32.

For some applications, switch 116 comprises an electromagnetic switch, which is controllable from outside the body of subject 84. Typically, external-unit control circuitry 106 is configured to cyclically drive switch 116 to switch between the first state and the second state. For example, external-unit control circuitry 106 may drive external coil 104 to generate a time-varying magnetic field at a first frequency to trigger the change in state of switch 116, and at a second frequency to generate the time-varying magnetic field that causes the current to flow through coiled wire 32 to generate the magnetic field that moves the one or more permanent magnets 44. Optionally, switch 116 comprises a small secondary coil 118 that is configured to receive the time-varying magnetic field having the first frequency.

Optionally, mechanical circulatory assist device 20 further comprises first and second capacitors 119A and 119B, arranged in parallel along respective first and second branches 114A and 114B of circuit 110. (As is known in the electronics art, a capacitor is a passive electrical component.)

Optionally, mechanical circulatory assist device 20 comprises additional passive electrical components, such as one or more resistors.

It is noted that the configuration of mechanical circulatory assist device 20 described with reference to FIG. 7 typically does not require the one or more springs 139 described hereinbelow with reference to FIGS. 8A-B.

Reference is now made to FIGS. 8A-B, which are schematic illustrations of a mechanical circulatory assist device 120, in accordance with an application of the present invention. Other than as described below, mechanical circulatory assist device 120 is identical to mechanical circulatory assist device 20, described hereinabove with reference to FIGS. 1-7, and may implement any of the features thereof, mutatis mutandis. Like reference numerals refer to like parts.

In this configuration, mechanical circulatory assist device 120 comprises:
- a circuit 210 in electrical communication with the two ends of coiled wire 32; and
- a passive diode 212, which is coupled in electrical communication with coiled wire 32, and is configured to rectify the current in coiled wire 32 such that the one or more permanent magnets 44 interact with the magnetic field generated by coiled wire 32, so as to axially move reciprocating valve 34 in a first direction with respect to stent 30 (downstream, as shown, or upstream (not shown)); and In this configuration, mechanical circulatory assist device 120 further comprises one or more springs 139, which are coupled to reciprocating valve 34 and stent 30, and are arranged to:
- store elastic energy during axial movement of reciprocating valve 34 in the first direction during interaction of the one or more permanent magnets 44 with the magnetic field generated by coiled wire 32, and
- axially move reciprocating valve 34 in a second direction, opposite the first direction, with respect to stent 30 upon release of the stored elastic energy when the current does not flow through coiled wire 32.

For some applications, the one or more springs 139 are coupled to housing stent 62 of housing 40 of reciprocating valve 34.

For some applications in which the first direction is downstream, such as shown, the one or more springs 139 are coupled to respective ones of the one or more downstream stoppers 72B (e.g., defined by some of stent struts 36 that are bent radially inward). For some other applications in which the first direction is upstream (not shown), the one or more springs 139 are coupled to respective ones of the one or more upstream stoppers 72A (e.g., defined by some of stent struts 36 that are bent radially inward).

Optionally, mechanical circulatory assist device 120 further comprises a capacitor 219, arranged in parallel with passive diode 212.

Figure 9:
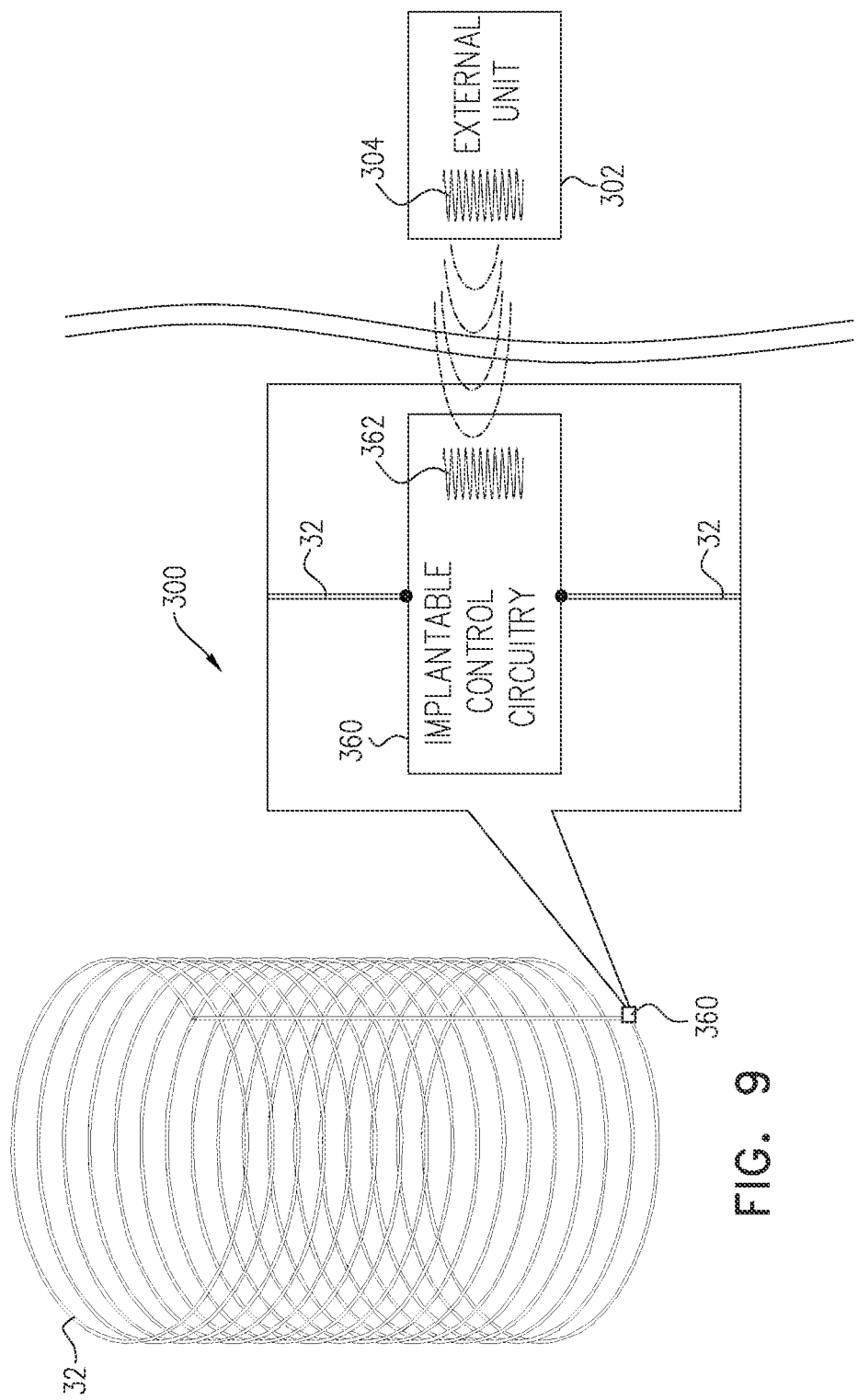
FIG. 9 is a schematic illustration of elements of a mechanical circulatory assist system, in accordance with an application of the present invention.

Reference is now made to FIG. 9, which is a schematic illustration of elements of a mechanical circulatory assist system 300, in accordance with an application of the present invention. Mechanical circulatory assist system 300 comprises an alternative configuration of mechanical circulatory assist device 20. In this configuration, mechanical circulatory assist device 20 comprises implantable control circuitry 360, which is in wired electrical connection with coiled wire 32, and is configured to generate the current in coiled wire 32. Implantable control circuitry 360 may comprise only passive electrical components, or may additionally comprise active electrical components. For clarity of illustration, the only elements of mechanical circulatory assist device 20 shown in FIG. 9 are coiled wire 32 and implantable control circuitry of 360.

Typically, implantable control circuitry 360 comprises a power-receiving coil 362, which is configured to wirelessly receive power transmitted by an external coil 304 of an external unit 302 of mechanical circulatory assist system 300.

Figure 10:
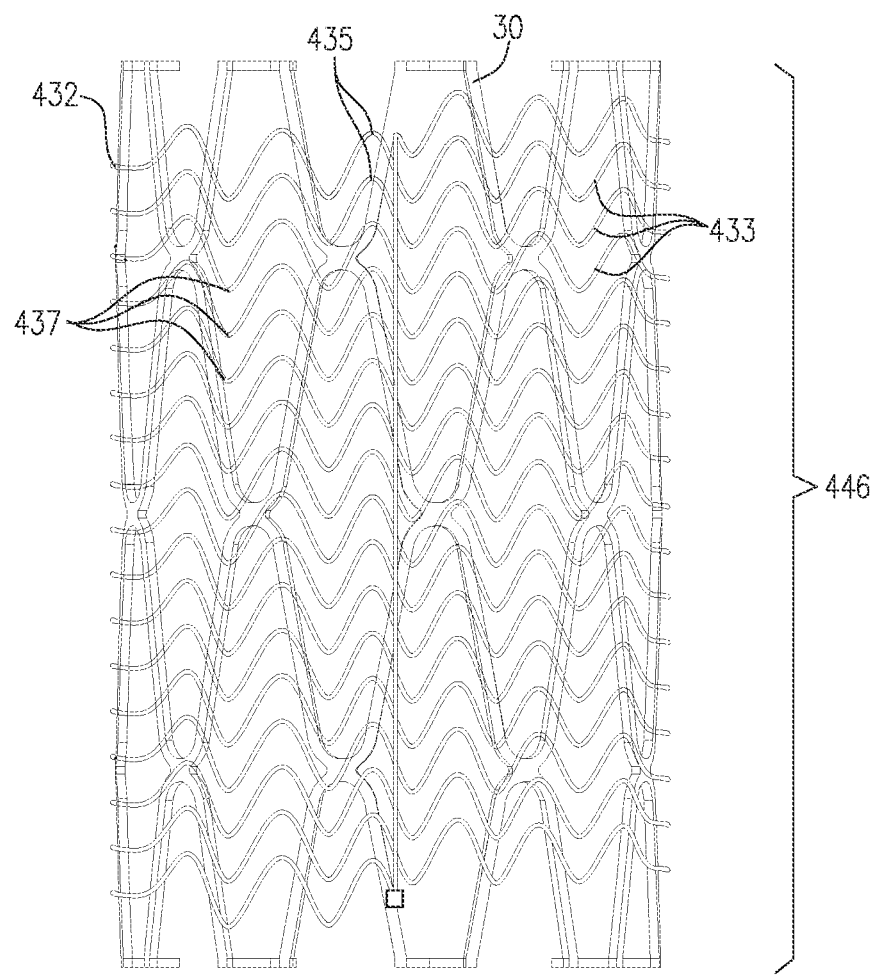
FIG. 10 is a schematic illustration of a coiled wire and a stent, in accordance with an application of the present invention.

Reference is now made to FIG. 10, which is a schematic illustration of a coiled wire 432 and stent 30, in accordance with an application of the present invention. Any of the mechanical circulatory assist devices described herein may comprise coiled wire 432 instead of coiled wire 32. Coiled wire 432 is shaped so as to define a plurality of wire turns 433. When stent 30 and coiled wire 432 are in the radially-expanded configuration of stent 30 and coiled wire 432, such as shown, wire turns 433 are shaped so as to define respective pluralities of peaks 435 and troughs 437, which are aligned with the respective peaks 435 and troughs 437 of longitudinally adjacent wire turns 433. This shape of coiled wire 432 may facilitate crimping of the coiled wire for disposal in a delivery sheath with stent 30 and coiled wire 432 in the radially-compressed configuration of stent 30 and coiled wire 432, such as in the above-mentioned first delivery sheath longitudinal segment 92A, and may also assist with radial expansion of the coiled wire upon delivery from the delivery sheath.

For some applications, each of the pluralities of peaks 435 and troughs 437 includes at least 3, such as at least 8, peaks 435 and at least 3, such as at least 8, troughs 437.

For some applications, the pluralities of peaks 435 and troughs 437 are shaped so as to define respective zigzags, such as shown.

Stent 30 and coiled wire 432 are typically elements of an assembly 446, which is cylindrical when stent 30 and coiled wire 432 are in the radially-expanded configuration of stent 30 and coiled wire 432. Assembly 446 is configured to assume a radially-compressed configuration when stent 30 and coiled wire 432 are in the radially-compressed configuration thereof.

Figure 11A:
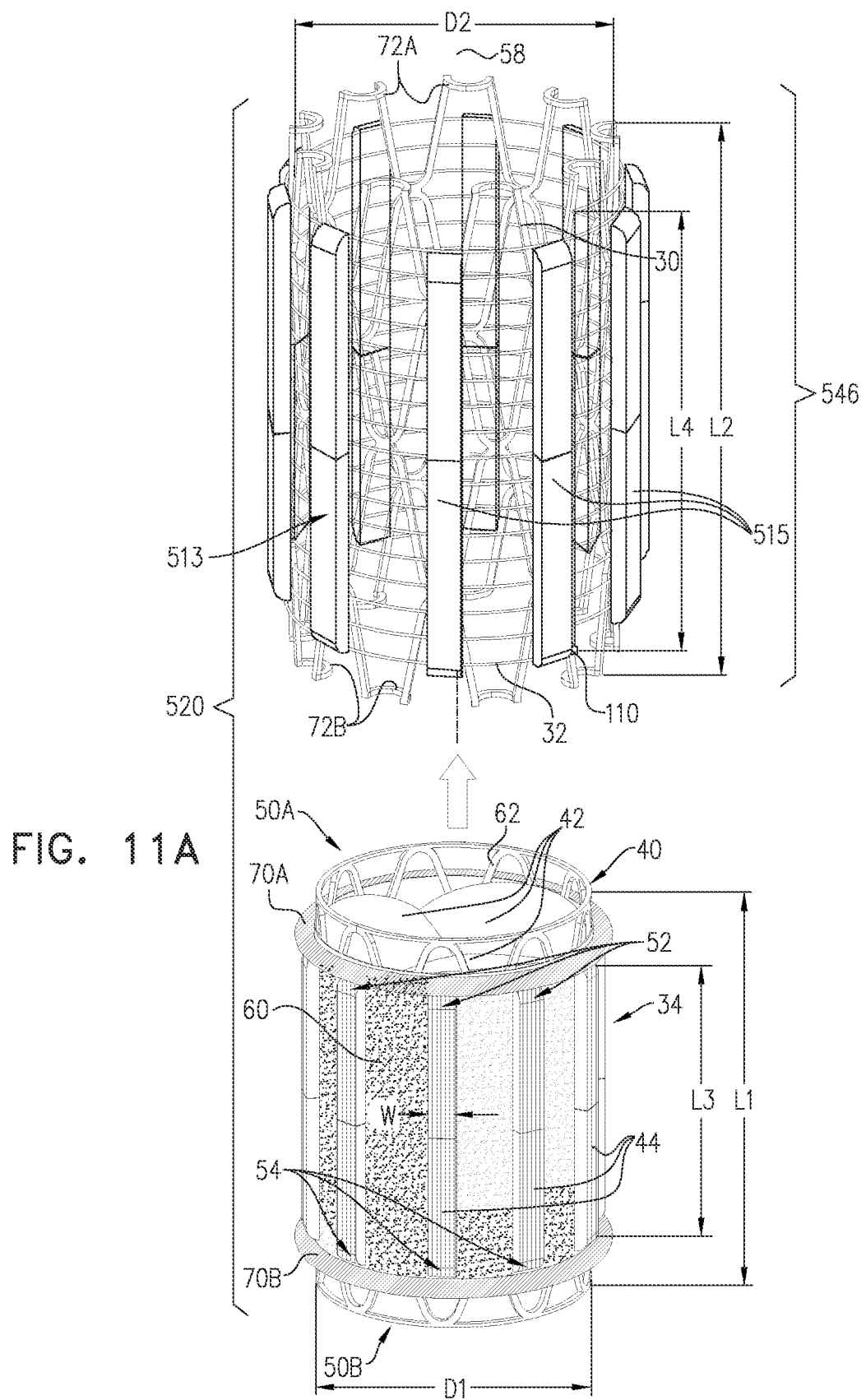
FIGS. 11A-B are schematic illustrations of yet another mechanical circulatory assist device, in accordance with an application of the present invention.
Figure 11B:
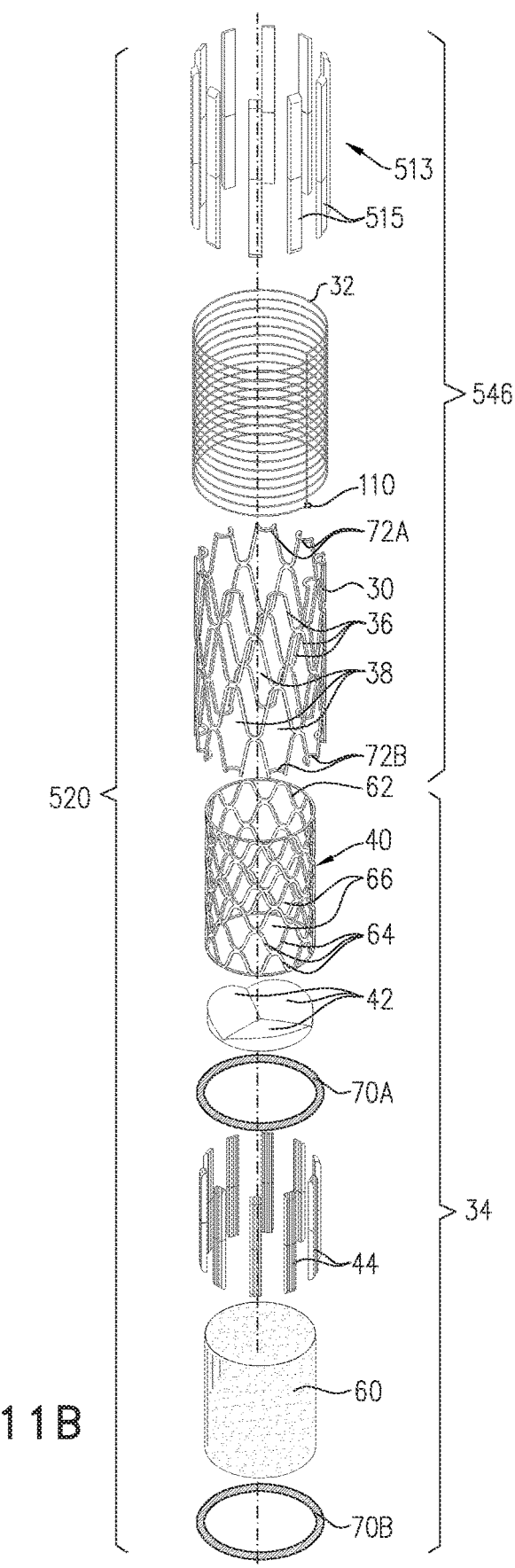

Reference is now made to FIGS. 11A-B, which are schematic illustrations of a mechanical circulatory assist device 520, in accordance with an application of the present invention. FIG. 11A shows mechanical circulatory assist device 520 before insertion of reciprocating valve 34 into stent 30. As mentioned above with reference to FIG. 4, in some applications of the present invention, reciprocating valve 34 and stent 30 are two separate pieces that are configured to be assembled together in situ during a deployment procedure, such as described hereinabove with reference to FIGS. 5A-D. For some of these applications, reciprocating valve 34 is configured to be inserted into stent 30 when stent 30 and coiled wire 32 are in the radially-expanded configuration of stent 30 and coiled wire 32 and reciprocating valve 34 is in the radially-compressed configuration of reciprocating valve 34. For clarity of illustration only, reciprocating valve 34 is shown in FIG. 11A in the radially-expanded configuration of reciprocating valve 34; in practice in this configuration, reciprocating valve 34 is actually inserted into stent 30 while reciprocating valve 34 is in the radially-compressed configuration of reciprocating valve 34, such as described hereinabove with reference to FIGS. 5C-D. FIG. 11B is a schematic exploded view of mechanical circulatory assist device 520 showing elements of the device.

Mechanical circulatory assist device 520 may implement any of the features of mechanical circulatory assist device 20, described hereinabove with reference to FIGS. 1-6E, and/or circulatory assist device 120, described hereinabove with reference to FIGS. 8A-B, mutatis mutandis, and like reference numerals refer to like parts. Optionally, mechanical circulatory assist device 520 comprises circuit 110, described hereinabove with reference to FIG. 7; alternatively, optionally, mechanical circulatory assist device 520 is an element of mechanical circulatory assist system 300, described hereinabove with reference to FIG. 9. For some applications, mechanical circulatory assist device 520 comprises coiled wire 432, described hereinabove with reference to FIG. 10, instead of coiled wire 32.

Mechanical circulatory assist device 520 further comprises openwork 513, which comprises a non-permanently-magnetized ferromagnetic metal. Openwork 513 is coupled to coiled wire 32 radially outward of coiled wire 32 (typically surrounding coiled wire 32) when stent 30 and coiled wire 32 are in the radially-expanded configuration of stent 30 and coiled wire 32. Openwork 513 is configured to assume a radially-compressed configuration (not shown) and a radially-expanded configuration (as shown) when stent 30 and coiled wire 32 are in the radially-compressed configuration and the radially-expanded configuration of stent 30 and coiled wire 32, respectively.

For example, the non-permanently-magnetized ferromagnetic metal may comprise iron, e.g., an iron alloy. Optionally, the ferromagnetic metal is soft, e.g., comprises soft iron. Optionally, the ferromagnetic metal is coated with a biocompatible coating, such as in configurations in which the ferromagnetic material comprises iron. Alternatively, the ferromagnetic metal is not coated with a biocompatible coating, such as in configuration in which the ferromagnetic metal comprises a biocompatible ferromagnetic material.

In this configuration, coiled wire 32 is typically wound around stent 30 outside stent 30 (as shown), although coiled wire 32 may alternatively be wound around stent 30 partially inside and partially outside stent 30 (configuration not shown). Optionally, openwork 513 is coupled to coiled wire 32 by being coupled to stent 30, such that the coiled wire 32 is sandwiched between stent 30 and openwork 513.

Providing openwork 513 helps concentrate the magnetic field generated by coiled wire 32, by reducing the length of the air gap to increase the efficiency of the circuit.

For some applications, when stent 30 and coiled wire 32 are in the radially-expanded configuration of stent 30 and coiled wire 32, an average axial length of openwork 513 is:
- 70%-110%, such as between 80%-100%, of the coil axial length L4,
- 70%-100%, such as 70%-90%, of the stent length L2, and/or
- 10-25 mm.

For some applications, openwork 513 comprises a plurality of elongate metal rods 515, which may or may not be interconnected with one another. Typically, elongate metal rods 515 are oriented parallel to axis 58 of stent 30 when stent 30 and coiled wire 32 are in the radially-expanded configuration of stent 30 and coiled wire 32.

Typically, openwork 513 comprises 10-30 elongate metal rods 515.

For some applications, when stent 30 and coiled wire 32 are in the radially-expanded configuration of stent 30 and coiled wire 32, an average rod length of elongate metal rods 515 is:
- 70%-110%, such as between 80%-100%, of the coil axial length L4,
- 70%-100%, such as 70%-90%, of the stent length L2, and/or
- 10-25 mm.

For some applications, when stent 30 and coiled wire 32 are in the radially-expanded configuration of stent 30 and coiled wire 32, elongate metal rods 515 have one or more respective widths, measured around a circumference of stent 30. For some applications, a sum of the one or more widths subtends 72-180 degrees, e.g., 90-150 degrees, such as 105-135 degrees, of a circumference of stent 30.

Alternatively, openwork 513 does not comprise elongate metal rods 515, and instead comprises, for example, a mesh, a stent (e.g., similar to stent 30), and/or another arrangement of metal that has openings that enable radial compression of openwork 513 (configurations not shown).

Stent 30, coiled wire 32, and openwork 513 are typically elements of an assembly 546, which is cylindrical when stent 30 and coiled wire 32 are in the radially-expanded configuration of stent 30 and coiled wire 32. Assembly 546 is configured to assume a radially-compressed configuration when stent 30 and coiled wire 32 are in the radially-compressed configuration thereof.

Figure 12:
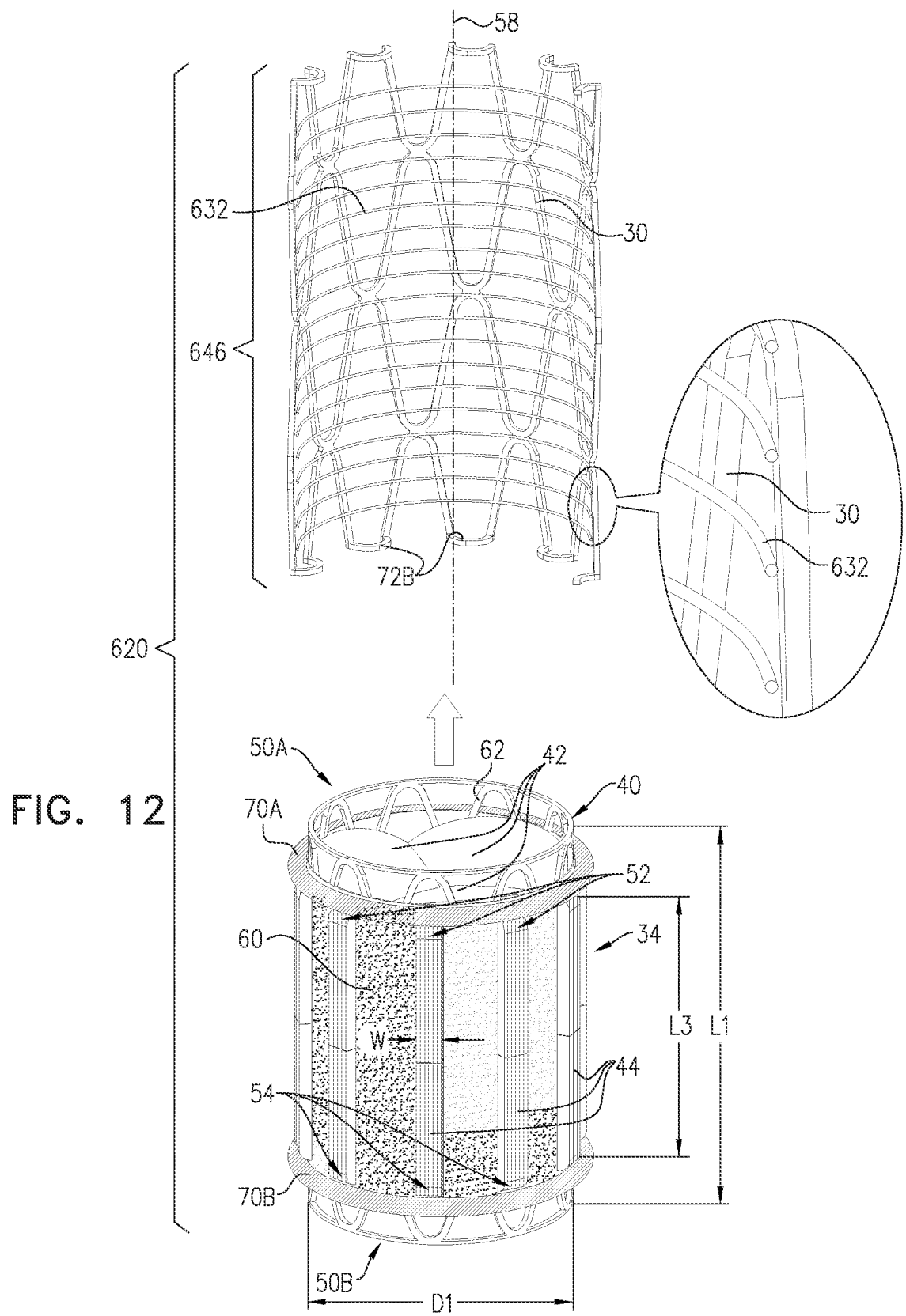
FIG. 12 is a schematic illustration of still another mechanical circulatory assist device, in accordance with an application of the present invention.

Reference is now made to FIG. 12, which is a schematic illustration of a mechanical circulatory assist device 620, in accordance with an application of the present invention. FIG. 12 shows mechanical circulatory assist device 620 before insertion of reciprocating valve 34 into stent 30. As mentioned above with reference to FIG. 4, in some applications of the present invention, reciprocating valve 34 and stent 30 are two separate pieces that are configured to be assembled together in situ during a deployment procedure, such as described hereinabove with reference to FIGS. 5A-D. For some of these applications, reciprocating valve 34 is configured to be inserted into stent 30 when stent 30 and coiled wire 32 are in the radially-expanded configuration of stent 30 and coiled wire 32 and reciprocating valve 34 is in the radially-compressed configuration of reciprocating valve 34. For clarity of illustration only, reciprocating valve 34 is shown in FIG. 12 in the radially-expanded configuration of reciprocating valve 34; in practice in this configuration, reciprocating valve 34 is actually inserted into stent 30 while reciprocating valve 34 is in the radially-compressed configuration of reciprocating valve 34, such as described hereinabove with reference to FIGS. 5C-D.

Mechanical circulatory assist device 620 may implement any of the features of mechanical circulatory assist device 20, described hereinabove with reference to FIGS. 1-6E, and/or circulatory assist device 120, described hereinabove with reference to FIGS. 8A-B, mutatis mutandis, and like reference numerals refer to like parts. Optionally, mechanical circulatory assist device 620 comprises circuit 110, described hereinabove with reference to FIG. 7; alternatively, optionally, mechanical circulatory assist device 620 is an element of mechanical circulatory assist system 300, described hereinabove with reference to FIG. 9. For some applications, mechanical circulatory assist device 620 comprises a coiled wire shaped like coiled wire 432, described hereinabove with reference to FIG. 10, instead of a coiled wire shaped like coiled wire 32 (as shown in FIG. 12).

Mechanical circulatory assist device 620 comprises a coiled wire 632 that is typically wound around stent 30 inside stent 30, although coiled wire 632 may alternatively be wound around stent 30 partially inside and partially outside stent 30, such as mostly inside stent 30 (configuration not shown). Stent 30 comprises a non-permanently-magnetized ferromagnetic metal, such as iron, e.g., an iron alloy. Optionally, the ferromagnetic metal is soft, e.g., comprises soft iron. Optionally, the ferromagnetic metal is coated with a biocompatible coating, such as in configurations in which the ferromagnetic material comprises iron. Alternatively, the ferromagnetic metal is not coated with a biocompatible coating, such as in configuration in which the ferromagnetic metal comprises a biocompatible ferromagnetic material.

Disposing coiled wire 632 within ferromagnetic stent 30 helps concentrate the magnetic field generated by coiled wire 632, by reducing the length of the air gap to increase the efficiency of the circuit.

Stent 30 and coiled wire 632 are typically elements of an assembly 646, which is cylindrical when stent 30 and coiled wire 632 are in the radially-expanded configuration of stent 30 and coiled wire 632. Assembly 646 is configured to assume a radially-compressed configuration when stent 30 and coiled wire 632 are in the radially-compressed configuration thereof.

Reference is now made to FIG. 13, which is a schematic illustration of a mechanical circulatory assist device 720 implanted at a native mitral valve 722 of the cardiovascular system, in accordance with an application of the present invention.

Other than as described below, mechanical circulatory assist device 720 is generally similar to the other mechanical circulatory assist devices described hereinabove. Mechanical circulatory assist device 720 may implement, mutatis mutandis, any of the features of mechanical circulatory assist device 20, described hereinabove with reference to FIGS. 1-6E; circulatory assist device 120, described hereinabove with reference to FIGS. 8A-B; circulatory assist device 520, described hereinabove with reference to FIGS. 11A-B; circulatory assist device 620, described hereinabove with reference to FIG. 12, and/or any of the other techniques described herein, such as with reference to FIGS. 7, 9, and/or 10. Like reference numerals refer to like parts.

Mechanical circulatory assist device 720 comprises a stent 730, a coiled wire 732, and a reciprocating valve 734, which may implement any of the features of the stents, coiled wires, and reciprocating valves described hereinabove, respectively, mutatis mutandis. Reciprocating valve 734 comprises one or more leaflets, which function as one or more prosthetic mitral leaflets upon implantation of the device at the native mitral valve. For some applications, stent 730 is configured, upon implantation, to push aside the native mitral leaflets, while for other applications, stent 730 is configured to be implanted above the native mitral leaflets.

For some applications, mechanical circulatory assist device 720 further comprises a circuit 710 in electrical communication with the two ends of coiled wire 732; for example, circuit 710 may implement any of the features of circuit 110, described hereinabove with reference to FIGS. 1, 2, and 4, or circuit 210, described hereinabove with reference to FIGS. 8A-B, mutatis mutandis.

Mechanical circulatory assist device 720 is typically shorter than the other mechanical circulatory assist devices described herein. For example:
  a housing 740 may have a housing length of 0.75-2 cm, such as 1-1.5 cm, and/or a housing outer diameter of 3-4.5 cm, when reciprocating valve 734 is in the radially-expanded configuration of reciprocating valve 734,
  stent 730 may have a stent length of 1-2 cm, such as 1-1.5 cm, when stent 730 and coiled wire 732 are in the radially-expanded configuration of stent 730 and coiled wire 732, and/or
  one or more permanent magnets 744 may have an average magnet length of 0.7-2 cm.

The elements of mechanical circulatory assist device 720 may have the relative dimensions described hereinabove for mechanical circulatory assist device 20 with reference to FIG. 4 (i.e., expressed as percentages of one another).

Mechanical circulatory assist device 720 is configured to be anchored to native mitral valve 722. Optionally, a stent 730 of mechanical circulatory assist device 720 assists with the anchoring when stent 730 and coiled wire 732 are in the radially-expanded configuration of stent 730 and coiled wire 732. Mechanical circulatory assist device 720 may alternatively or additionally comprise additional anchoring elements, such as, for example, hooks 741, such as those known in the prosthetic mitral valve art, including the transcatheter prosthetic mitral valve art.

Mechanical circulatory assist device 720 is typically configured to treat diastolic heart failure, in which a left ventricle 726 is not able to fill properly with blood during diastole. Mechanical circulatory assist device 720 augments filling during diastole by increasing filling pressure and volume, as described below.

Reference is still made to FIG. 13. For some applications, a mechanical circulatory assist system 700 is provided that comprises mechanical circulatory assist device 720 and an external unit 702, which comprises external coil 104 and external-unit control circuitry 706, which is configured to drive external coil 104 to generate the time-varying magnetic field. Mechanical circulatory assist system 700 may implement any of the techniques of mechanical circulatory assist system 100, described hereinabove with reference to FIG. 5D, and/or mechanical circulatory assist system 300, described hereinabove with reference to FIG. 9.

For some applications, mechanical circulatory assist system 700 is configured to be operated in a synchronous pattern with respect to the cardiac cycle. To this end, mechanical circulatory assist system 700 comprises a sensor 721 configured to sense at least one physiological parameter correlated with the cardiac cycle, such as left ventricular pressure (LVP) or a feature of an ECG. For some applications, mechanical circulatory assist device 720 comprises sensor 721, such as shown. For example, sensor 721 may be located at or near a downstream end of stent 730, such that the sensor is disposed within ventricle 726 upon implantation of mechanical circulatory assist device 720. For other applications, external unit 702 comprises sensor 721, such as in configurations in which sensor 721 is an ECG sensor (configuration not shown).

For some applications, mechanical circulatory assist system 700 is configured to synchronize pumping of reciprocating valve 734 with respect to the physiological parameter sensed with sensor 721. In particular, mechanical circulatory assist system 700 is typically configured to activate motion of reciprocating valve 734 only during all or a portion of diastole detected using sensor 721. It is noted that relatively low power is required for the device to pump during diastole, because the pump stroke typically needs to overcome only 10-25 mmHg. This synchronization may be performed by circuit 710 of mechanical circulatory assist device 720, by external-unit control circuitry 706, or by circuit 710 and external-unit control circuitry 706 in combination. As mentioned above, systole and diastole, as used herein, including in the claims and Inventive Concepts, mean ventricular systole and ventricular diastole, respectively.

For some applications, mechanical circulatory assist system 700 is configured to begin pumping a period of time before the end of diastole; for example, the period of time may be between 200 and 300 ms. Mechanical circulatory assist system 700 may be configured to continue pumping until the conclusion of diastole, typically replacing the natural atrial kick (atrial contraction). Mechanical circulatory assist system 700 may be configured to pump for several strokes during this portion of diastole each cardiac cycle.

For example, mechanical circulatory assist system 700 may be configured to begin pumping a predetermined wait period after detecting, using sensor 721, that LVP has crossed a threshold value, e.g., a value of 10-15 mmHg, or detecting a P-wave of the cardiac cycle, using sensor 721. For example, the predetermined wait period may be 150-250 ms, e.g., 200 ms.

For example, mechanical circulatory assist system 700 may be configured to pump for a predetermined amount of time, e.g., between 250-350 ms, such as 300 ms.

In this configuration, mechanical circulatory assist system 700 is typically configured not to activate reciprocating valve 734 during systole.

For other applications, mechanical circulatory assist system 700 is not configured to synchronize pumping of reciprocating valve 734 with respect to the cardiac cycle of the subject. For example, external-unit control circuitry 706 is not configured to drive external coil 104 to generate the time-varying magnetic field in coordination with the cardiac cycle of the subject. Thus, for these applications, mechanical circulatory assist system 700 typically does not comprise sensor 721 (or any other sensor of heart rate or cardiac cycle). In these applications, mechanical circulatory assist system 700 is configured to periodically drive motion of reciprocating valve 734 with respect to housing 740. Typically, some of the strokes of the valve occur during diastole and some of the strokes of the valve occur during systole. However, reciprocating valve 734 is not activated with sufficient power to pump during systole. As a result, pumping occurs only during diastole, in order to treat diastolic heart failure, in which left ventricle 726 is not able to fill properly with blood during diastole.

Optionally, mechanical circulatory assist system 700 is configured to operate reciprocating valve 734 only when the subject is awake.

Optionally, mechanical circulatory assist system 700 further comprises an activity sensor, and is configured to operate reciprocating valve 734 only upon sensing a threshold level of activity of the subject, or to set a higher rate of pumping at higher levels of sensed activity of the subject.

It is noted that if mechanical circulatory assist system 700 were to be disabled or to malfunction, the one or more leaflets of circulatory assist device 720 would function like native mitral leaflets and continue to open and close during the cardiac cycle based on the natural pressure gradients across the mitral valve.

Although the devices described herein have been described as providing mechanical circulatory assistance, they may alternatively serve other purposes when implanted in blood vessels or other body lumens or cavities, and thus not comprise a reciprocating valve. The magnetically-driven motion of an inner component of the devices may instead provide mechanical energy for other purposes.

In an embodiment, techniques and apparatus described in one or more of the following patents and/or applications, which are assigned to the assignee of the present application and are incorporated herein by reference, are combined with techniques and apparatus described herein:

U.S. Pat. No. 10,568,999 to Gross
U.S. Pat. No. 11,013,906 to Gross
European Patent Application Publication EP 3733223 A1 to Gross In case of conflict between definitions provided herein and those provided in the patents and patent application publication incorporated herein by reference, the definitions provided herein will prevail.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A mechanical circulatory assist device configured to be deployed in a cardiovascular system of a subject, the mechanical circulatory assist device comprising:
   (a) a stent;
   (b) a coiled wire, which is wound around the stent inside, outside, or partially inside and partially outside the stent,
      wherein the stent and the coiled wire are configured to assume a radially-compressed configuration and a radially-expanded configuration,
      wherein the coiled wire is shaped so as to define a plurality of wire turns, and wherein all of the wire turns encircle a same, single central longitudinal axis of the stent when the stent and the coiled wire are in the radially-expanded configuration of the stent and the coiled wire, and
      wherein the plurality of wire turns of the coiled wire are configured to generate a magnetic field when current flows through the coiled wire when the stent and the coiled wire are in the radially-expanded configuration of the stent and the coiled wire; and
   (c) a reciprocating valve, which is configured to assume radially-compressed and radially-expanded configurations, and which comprises:
      (i) a housing;
      (ii) one or more leaflets, coupled to the housing; and
      (iii) one or more permanent magnets, which are coupled to the housing, and are arranged to interact with the magnetic field generated by the plurality of wire turns of the coiled wire, so as to axially move the reciprocating valve with respect to the stent when the reciprocating valve is in the radially-expanded configuration of the reciprocating valve disposed within the stent when the stent and the coiled wire are in the radially-expanded configuration of the stent and the coiled wire,
      wherein the reciprocating valve is configured such that:
         upstream axial motion of the reciprocating valve causes the one or more leaflets to be in an open state in which the one or more leaflets allow blood flow through the reciprocating valve, and
         downstream axial motion of the reciprocating valve causes the one or more leaflets to be in a closed state in which the one or more leaflets inhibit blood flow through the reciprocating valve.

2. The mechanical circulatory assist device according to claim 1, wherein the one or more permanent magnets are arranged to interact with the magnetic field generated by the coiled wire, so as to axially slide the reciprocating valve with respect to the stent when the reciprocating valve is in the radially-expanded configuration of the reciprocating valve disposed within the stent when the stent and the coiled wire are in the radially-expanded configuration of the stent and the coiled wire.

3. The mechanical circulatory assist device according to claim 1, wherein the reciprocating valve is configured to be inserted into the stent when the stent and the coiled wire are in the radially-expanded configuration of the stent and the coiled wire and the reciprocating valve is in the radially-compressed configuration of the reciprocating valve.

4. The mechanical circulatory assist device according to claim 1, wherein the mechanical circulatory assist device does not comprise any active electronic components.

5. The mechanical circulatory assist device according to claim 1, wherein the mechanical circulatory assist device is configured to be deployed in a blood vessel of the cardiovascular system.

6. The mechanical circulatory assist device according to claim 1, wherein the mechanical circulatory assist device is configured to be deployed at a mitral valve of the cardiovascular system.

7. A mechanical circulatory assist system comprising the mechanical circulatory assist device according to claim 6, wherein the coiled wire is configured such that the current is electromagnetically induced in the coiled wire when the coiled wire is subjected to a time-varying magnetic field generated outside a body of the subject when the stent and the coiled are in the radially-expanded configuration of the stent and the coiled wire, with the mechanical circulatory assist device deployed at the mitral valve,
wherein the mechanical circulatory assist system further comprises an external unit, which comprises:
an external coil, which is configured to be placed outside the body of the subject; and
external-unit control circuitry, which is configured to drive the external coil to generate the time-varying magnetic field,
wherein the mechanical circulatory assist system comprises a sensor configured to sense at least one physiological parameter correlated with a cardiac cycle of the subject, and
wherein the mechanical circulatory assist system is configured to coordinate pumping of the reciprocating valve with the at least one physiological parameter sensed by the sensor.

8. The mechanical circulatory assist system according to claim 7, wherein the mechanical circulatory assist system is configured to activate motion of the reciprocating valve only during all or a portion of diastole, as detected using the sensor.

9. The mechanical circulatory assist system according to claim 8, wherein the mechanical circulatory assist system is configured to activate the motion of the reciprocating valve in a plurality of strokes during diastole of each cardiac cycle, wherein each of the strokes includes the upstream axial motion and the downstream axial motion of the reciprocating valve.

10. A mechanical circulatory assist system comprising the mechanical circulatory assist device according to claim 6,
wherein the coiled wire is configured such that the current is electromagnetically induced in the coiled wire when the coiled wire is subjected to a time-varying magnetic field generated outside a body of the subject when the stent and the coiled are in the radially-expanded configuration of the stent and the coiled wire, with the mechanical circulatory assist device deployed at the mitral valve,
wherein the mechanical circulatory assist system further comprises an external unit, which comprises:
an external coil, which is configured to be placed outside the body of the subject; and
external-unit control circuitry, which is configured to drive the external coil to generate the time-varying magnetic field, and which is not configured to drive the external coil to generate the time-varying magnetic field in coordination with a cardiac cycle of the subject.

11. The mechanical circulatory assist device according to claim 1, wherein the coiled wire is configured such that the current is electromagnetically induced in the coiled wire when the coiled wire is subjected to a time-varying magnetic field generated outside a body of the subject when the stent and the coiled are in the radially-expanded configuration of the stent and the coiled wire, with the mechanical circulatory assist device deployed in the cardiovascular system.

12. The mechanical circulatory assist device according to claim 11, further comprising:
a passive diode, which is coupled in electrical communication with the coiled wire, and is configured to rectify the current in the coiled wire such that the one or more permanent magnets interact with the magnetic field generated by the coiled wire, so as to axially move the reciprocating valve in a first direction with respect to the stent; and
one or more springs, which are coupled to the reciprocating valve and the stent, and are arranged to:
store elastic energy during axial movement of the reciprocating valve in the first direction during interaction of the one or more permanent magnets with the magnetic field generated by the coiled wire, and
axially move the reciprocating valve in a second direction, opposite the first direction, with respect to the stent upon release of the stored elastic energy when the current does not flow through the coiled wire.

13. A mechanical circulatory assist system comprising the mechanical circulatory assist device according to claim 11, the mechanical circulatory assist system further comprising an external unit, which comprises:
an external coil, which is configured to be placed outside the body of the subject; and
external-unit control circuitry, which is configured to drive the external coil to generate the time-varying magnetic field.

14. The mechanical circulatory assist system according to claim 13, wherein the external-unit control circuitry is configured to drive the external coil to generate the time-varying magnetic field at a frequency of 5.6-14 MHz.

15. The mechanical circulatory assist system according to claim 13, wherein the external-unit control circuitry is configured to drive the external coil to generate the time-varying magnetic field such that the reciprocating valve reciprocates at a frequency of 2-5 Hz.

16. The mechanical circulatory assist system according to claim 13, wherein the external-unit control circuitry is not configured to drive the external coil to generate the time-varying magnetic field in coordination with a cardiac cycle of the subject.

17. The mechanical circulatory assist system according to claim 13,
wherein the mechanical circulatory assist device further comprises:
a circuit in electrical communication with the coiled wire;
first and second passive diodes, which are (a) arranged in parallel along respective first and second branches of the circuit, and (b) configured to rectify the current in the respective branches in respective opposite first and second directions; and
a switch, which is arranged to selectively assume first and second states, in which the switch electrically couples only the first branch and only the second branch, respectively, to the coiled wire, and
wherein the external-unit control circuitry is configured to cyclically drive the switch to switch between the first state and the second state.

18. The mechanical circulatory assist device according to claim 1,
wherein the coiled wire is configured such that the current is electromagnetically induced in the coiled wire when the coiled wire is subjected to a time-varying magnetic field generated outside a body of the subject when the stent and the coiled wire are in the radially-expanded configuration of the stent and the coiled wire, with the mechanical circulatory assist device deployed in the cardiovascular system,
the mechanical circulatory assist device further comprising:
a circuit in electrical communication with the coiled wire;
first and second passive diodes, which are (a) arranged in parallel along respective first and second branches of the circuit, and (b) configured to rectify the current in the respective branches in respective opposite first and second directions; and
a switch, which is arranged to selectively assume first and second states, in which the switch electrically couples only the first branch and only the second branch, respectively, to the coiled wire.

19. The mechanical circulatory assist device according to claim 1, wherein, when the stent and the coiled wire are in the radially-expanded configuration of the stent and the coiled wire:
the wire turns are shaped so as to define respective pluralities of peaks and troughs, which are aligned with the respective peaks and troughs of longitudinally adjacent wire turns.

20. The mechanical circulatory assist device according to claim 1, wherein the reciprocating valve further comprises a blood-proof membrane that is tubular when the reciprocating valve is in the radially-expanded configuration of the reciprocating valve.

21. The mechanical circulatory assist device according to claim 1, wherein the stent, when the stent and the coiled wire are in the radially-expanded configuration of the stent and the coiled wire, is shaped so as to define one or more upstream stoppers, which are configured to limit the upstream axial motion of the reciprocating valve when in the radially-expanded configuration of the reciprocating valve disposed within the stent.

22. The mechanical circulatory assist device according to claim 21, wherein the reciprocating valve further comprises an upstream seal that is annular when the reciprocating valve is in the radially-expanded configuration of the reciprocating valve, and wherein the one or more upstream stoppers are configured to limit the upstream axial motion of the reciprocating valve by contacting and blocking upstream axial motion of the upstream seal.

23. The mechanical circulatory assist device according to claim 1, further comprising openwork, which (a) comprises a non-permanently-magnetized ferromagnetic metal, (b) is coupled to the coiled wire radially outward of the coiled wire when the stent and the coiled wire are in the radially-expanded configuration of the stent and the coiled wire, and (c) is configured to assume a radially-compressed configuration and a radially-expanded configuration.

24. The mechanical circulatory assist device according to claim 23, wherein the non-permanently-magnetized ferromagnetic metal comprises soft iron.

25. The mechanical circulatory assist device according to claim 23, wherein the openwork comprises a plurality of elongate metal rods.

26. The mechanical circulatory assist device according to claim 25, wherein the elongate metal rods are not interconnected with one another.

27. The mechanical circulatory assist device according to claim 25, wherein the elongate metal rods are oriented parallel to the same, single central longitudinal axis of the stent when the stent and the coiled wire are in the radially-expanded configuration of the stent and the coiled wire.

28. The mechanical circulatory assist device according to claim 1, wherein the stent comprises a non-permanently-magnetized ferromagnetic metal.

29. The mechanical circulatory assist device according to claim 28, wherein the non-permanently-magnetized ferromagnetic metal comprises soft iron.

30. The mechanical circulatory assist device according to claim 28, wherein the coiled wire is wound around the stent inside the stent.

31. A mechanical circulatory assist system comprising the mechanical circulatory assist device according to claim 1, the mechanical circulatory assist system further comprising first and second delivery sheath longitudinal segments,
wherein the stent and the coiled wire are removably disposed in the first delivery sheath longitudinal segment with the stent and the coiled wire in the radially-compressed configuration of the stent and the coiled wire, and
wherein the reciprocating valve is removably disposed in the second delivery sheath longitudinal segment in the radially-compressed configuration of the reciprocating valve.

32. The mechanical circulatory assist device according to claim 1, further comprising implantable control circuitry, which is in wired electrical connection with the coiled wire, and is configured to generate the current in the coiled wire.

33. A mechanical circulatory assist system comprising the mechanical circulatory assist device according to claim 32,
the mechanical circulatory assist system further comprising an external unit, which comprises an external coil configured to wirelessly transmit power,
wherein the implantable control circuitry comprises a power-receiving coil, which is configured to wirelessly receive the power transmitted by the external coil of the external unit.

34. The mechanical circulatory assist device according to claim 1, wherein the plurality of wire turns includes 10-100 wire turns.

35. The mechanical circulatory assist device according to claim 1,
wherein the mechanical circulatory assist device comprises exactly one coiled wire that is wound around the stent inside, outside, or partially inside and partially outside the stent, and is shaped so as to define the plurality of wire turns.

36. A method comprising:
delivering, to a location in a cardiovascular system of a subject, a mechanical circulatory assist device while a stent and a coiled wire of the mechanical circulatory assist device are in a radially-compressed configuration and a reciprocating valve of the mechanical circulatory assist device is in a radially-compressed configuration,
wherein the coiled wire is wound around the stent inside, outside, or partially inside and partially outside the stent,
wherein the coiled wire is shaped so as to define a plurality of wire turns, and wherein all of the wire turns encircle a same, single central longitudinal axis of the stent when the stent and the coiled wire are in the radially-expanded configuration of the stent and the coiled wire, and wherein the plurality of wire turns of the coiled wire are configured to generate a magnetic field when current flows through the coiled wire when the stent and the coiled wire are in a radially-expanded configuration of the stent and the coiled wire; and transitioning (a) the stent and the coiled wire to the radially-expanded configuration of the stent and the coiled wire, and (b) the reciprocating valve to a radially-expanded configuration of the reciprocating valve, wherein the reciprocating valve includes (i) a housing; (ii) one or more leaflets, coupled to the housing; and (iii) one or more permanent magnets, which are coupled to the housing, and are arranged to interact with the magnetic field generated by the plurality of wire turns of the coiled wire, so as to axially move the reciprocating valve with respect to the stent when the reciprocating valve is in the radially-expanded configuration of the reciprocating valve disposed within the stent when the stent and the coiled wire are in the radially-expanded configuration of the stent and the coiled wire, and wherein the reciprocating valve is configured such that:
upstream axial motion of the reciprocating valve causes the one or more leaflets to be in an open state in which the one or more leaflets allow blood flow through the reciprocating valve, and downstream axial motion of the reciprocating valve causes the one or more leaflets to be in a closed state in which the one or more leaflets inhibit blood flow through the reciprocating valve.

37. The method according to claim 36, wherein the mechanical circulatory assist device includes exactly one coiled wire that is wound around the stent inside, outside, or partially inside and partially outside the stent, and is shaped so as to define the plurality of wire turns.

* * * * *